(12) United States Patent
Novak et al.

(10) Patent No.: US 10,035,719 B2
(45) Date of Patent: Jul. 31, 2018

(54) SYSTEM AND MEMBRANE FOR WASTEWATER-GENERATED ENERGY AND GAS

(71) Applicant: Regents of the University of Minnesota, Minneapolis, MN (US)

(72) Inventors: Paige J. Novak, St. Paul, MN (US); William Alan Arnold, Minnetonka, MN (US); Alptekin Aksan, Minneapolis, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 376 days.

(21) Appl. No.: 14/884,407

(22) Filed: Oct. 15, 2015

(65) Prior Publication Data

US 2016/0107912 A1 Apr. 21, 2016

Related U.S. Application Data

(60) Provisional application No. 62/064,183, filed on Oct. 15, 2014.

(51) Int. Cl.
*C02F 3/34* (2006.01)
*C02F 11/04* (2006.01)
(Continued)

(52) U.S. Cl.
CPC .............. *C02F 3/348* (2013.01); *C02F 3/102* (2013.01); *C02F 3/108* (2013.01); *C02F 3/109* (2013.01);
(Continued)

(58) Field of Classification Search
CPC .......... C02F 3/348; C02F 3/341; C02F 3/109; C02F 3/108; C02F 3/102; C02F 2103/002;
(Continued)

(56) References Cited

U.S. PATENT DOCUMENTS 4,010,076 A * 3/1977 Weetall .................. A01G 33/00
435/168
4,148,689 A 4/1979 Hino et al.
(Continued)

FOREIGN PATENT DOCUMENTS

CN 1715182 A 1/2006
WO WO-02/10218 A1 2/2002
(Continued)

OTHER PUBLICATIONS

Energy Production with Immobilized Cells, Shuichi Suzuki and Isao Karube Applied Biochemistry and Bioengineering vol. 4 p. 281-310 (1983).*
(Continued)

*Primary Examiner* — Pamela H Weiss
(74) *Attorney, Agent, or Firm* — Schwegman Lundberg & Woessner, P.A.

(57) ABSTRACT

Systems and methods for producing and extracting a gas from a wastewater fluid including multiple sheets or layers that form a composite membrane. The composite membrane includes a sandwich structure in which a dry matrix layer is surrounded by a first layer including a first immobilized bacteria and a second layer including a second immobilized bacteria. The first immobilized bacteria and the second immobilized bacteria can be configured to produce a gas from one or more compounds in a wastewater fluid. The dry matrix layer can be configured to receive the gas from the first and second layers, and the gas can be extracted from the membrane. The hydrophobic coatings can be disposed between the dry matrix layer and one or both of the first and second layers. An adhesive interface can be disposed between the dry matrix layer and one or both of the first and second layers.

20 Claims, 13 Drawing Sheets

(51) Int. Cl.

| | | |
|---|---|---|
| *C12M 1/107* | (2006.01) | |
| *C02F 3/30* | (2006.01) | |
| *B01D 69/12* | (2006.01) | |
| *B01D 71/02* | (2006.01) | |
| *B01D 71/38* | (2006.01) | |
| *C12M 1/12* | (2006.01) | |
| *C12M 1/04* | (2006.01) | |
| *C12M 1/00* | (2006.01) | |
| *C02F 3/10* | (2006.01) | |
| *C02F 103/20* | (2006.01) | |
| *C02F 103/26* | (2006.01) | |
| *C02F 103/00* | (2006.01) | |

(52) U.S. Cl.
CPC .............. *C02F 3/341* (2013.01); *C12M 21/04* (2013.01); *C12M 23/20* (2013.01); *C12M 23/24* (2013.01); *C12M 23/40* (2013.01); *C12M 25/02* (2013.01); *C02F 2103/001* (2013.01); *C02F 2103/002* (2013.01); *C02F 2103/005* (2013.01); *C02F 2103/20* (2013.01); *C02F 2103/26* (2013.01); *C02F 2203/006* (2013.01); *C02F 2303/10* (2013.01); *Y02E 50/343* (2013.01); *Y02W 10/15* (2015.05); *Y02W 10/30* (2015.05)

(58) Field of Classification Search
CPC .......... C02F 2103/001; C02F 2203/006; C02F 2103/26; C02F 2303/10; C02F 2103/20; C12M 23/40; C12M 23/24; C12M 25/02; C12M 21/04; C12M 23/20; Y02W 10/15; Y02W 10/30; Y02E 50/343
See application file for complete search history.

(56) References Cited

U.S. PATENT DOCUMENTS

| | | | |
|---|---|---|---|
| 4,391,909 A | 7/1983 | Lim | |
| 5,200,334 A | 4/1993 | Dunn et al. | |
| 5,229,096 A | 7/1993 | Cohen | |
| 5,252,318 A | 10/1993 | Joshi et al. | |
| 5,416,022 A | 5/1995 | Amiot | |
| 5,508,193 A | 4/1996 | Mandelbaum et al. | |
| 5,693,513 A | 12/1997 | Pope | |
| 5,739,020 A | 4/1998 | Pope | |
| 6,214,593 B1 | 4/2001 | Carturan et al. | |
| 6,248,321 B1 | 6/2001 | Winder et al. | |
| 6,284,522 B1 | 9/2001 | Wackett et al. | |
| 6,303,290 B1 | 10/2001 | Liu | |
| 6,369,299 B1 | 4/2002 | Sadowsky et al. | |
| 6,495,352 B1 | 12/2002 | Brinker et al. | |
| 6,673,582 B2 | 1/2004 | McTavish | |
| 6,825,001 B2 | 11/2004 | Wackett et al. | |
| 6,979,464 B2 | 12/2005 | Gutowska | |
| 7,033,571 B2 | 4/2006 | Gutowska et al. | |
| 7,052,913 B2 | 5/2006 | Babich et al. | |
| 7,204,997 B2 | 4/2007 | Bromberg et al. | |
| 7,510,656 B2 | 3/2009 | Shafer et al. | |
| 8,337,923 B2 | 12/2012 | Coyne et al. | |
| 8,367,109 B2 | 2/2013 | Chidambaram et al. | |
| 9,534,236 B2 * | 1/2017 | Novak .................... | C02F 3/102 |
| 9,790,484 B2 * | 10/2017 | Wackett ................. | C12N 11/14 |
| 2001/0055797 A1 | 12/2001 | Conroy | |
| 2005/0009159 A1 | 1/2005 | Paterek | |
| 2005/0095690 A1 | 5/2005 | Naik et al. | |
| 2006/0171990 A1 | 8/2006 | Asgari | |
| 2009/0061496 A1 | 3/2009 | Kuhn et al. | |
| 2009/0075354 A1 | 3/2009 | Reneker et al. | |
| 2009/0136932 A1 | 5/2009 | Craighead et al. | |
| 2009/0220378 A1 | 9/2009 | McDonnell et al. | |
| 2009/0221047 A1 | 9/2009 | Schindler et al. | |
| 2009/0258051 A1 | 10/2009 | Chidambaram et al. | |
| 2009/0300745 A1 | 12/2009 | Dispensa | |
| 2009/0305412 A1 | 12/2009 | Ying et al. | |
| 2010/0055154 A1 | 3/2010 | Liao et al. | |
| 2010/0190666 A1 | 7/2010 | Ali et al. | |
| 2011/0165811 A1 | 7/2011 | Hill et al. | |
| 2011/0259804 A1 | 10/2011 | Reitzel et al. | |
| 2012/0107900 A1 | 5/2012 | Greiner et al. | |
| 2012/0205041 A1 | 8/2012 | Dalborg | |
| 2012/0263771 A1 | 10/2012 | Carlson et al. | |
| 2014/0051144 A1 | 2/2014 | Wackett et al. | |
| 2014/0256007 A1 | 9/2014 | Novak et al. | |
| 2014/0335148 A1 | 11/2014 | Tong et al. | |
| 2015/0017683 A1 | 1/2015 | Abdullah et al. | |

FOREIGN PATENT DOCUMENTS

| | | | |
|---|---|---|---|
| WO | WO-2007/129991 A1 | 11/2007 | |
| WO | WO-2008/028194 A2 | 3/2008 | |
| WO | WO-2008/075824 A1 | 6/2008 | |
| WO | WO-2010/112820 A1 | 10/2010 | |
| WO | WO-2011/011468 A2 | 5/2011 | |
| WO | WO-2012/064287 A1 | 5/2012 | |
| WO | WO-2012/116013 A2 | 8/2012 | |
| WO | WO-2012/116013 A3 | 8/2012 | |
| WO | WO 2012116013 A2 * | 8/2012 | .............. C02F 3/108 |
| WO | WO-2013/070778 A1 | 5/2013 | |
| WO | WO-2014/182799 A1 | 11/2014 | |

OTHER PUBLICATIONS

Methane Production from Organic Acid Rich Wastewaters by immobilized thermophilic methane producing bacteria Tadashi Matsunaga Isao Karube Shuichi Suzuki; Enzyme Mcorb Technol (1983) vol. 4 Nov. pp. 441-444.*

Methane Production from Wastewaters by Immobilized Methanogenic Bacteria; Isao Karube, Shinichi Kuriyama Tadashi Matsunaga and Shuichi Suzuki Biotechnology and Bioengineering vol. XXII, pp. 847-857 (1980).*

"Canadian Application Serial No. 2,827,559, Office Action dated Mar. 13, 2017", 4 pgs.

"U.S. Appl. No. 14/001,094, Notice of Allowance dated Jul. 13, 2017", 9 pgs.

"U.S. Appl. No. 14/001,094, Response filed Mar. 13, 2017 to Final Office Action dated Dec. 15, 2016", 17 pgs.

"U.S. Appl. No. 14/001,094, Non Final Office Action dated Dec. 15, 2016", 11 pgs.

"U.S. Appl. No. 14/198,104, PTO Response to Rule 312 Communication dated Dec. 5, 2016", 4 pgs.

"Australian Application Serial No. 2012220738, First Examiner Report dated Oct. 5, 2016", 3 pgs.

"U.S. Appl. No. 14/001,094, Response filed Oct. 4, 2016 to Final Office Action dated Aug. 4, 2016", 13 pgs.

"U.S. Appl. No. 14/198,104, Notice of Allowance dated Jul. 29, 2016", 8 pgs.

"U.S. Appl. No. 14/001,094, Final Office Action dated Aug. 4, 2016", 10 pgs.

"U.S. Appl. No. 14/001,094, Response filed Nov. 12, 2015 to Restriction Requirement dated Sep. 17, 2015", 9 pgs.

"U.S. Appl. No. 14/001,094, Non Final Office Action dated Dec. 31, 2015", 10 pgs.

"U.S. Appl. No. 14/001,094, Response filed Mar. 24, 2016 to Non Final Office Action dated Dec. 31, 2015", 15 pgs.

"U.S. Appl. No. 14/001,094, Restriction Requirement dated Sep. 17, 2015", 6 pgs.

"U.S. Appl. No. 14/198,104, Non Final Office Action dated Jan. 11, 2016", 13 pgs.

"U.S. Appl. No. 14/198,104, Response filed May 11, 2016 to Non Final Office Action dated Jan. 11, 2016", 15 pgs.

"U.S. Appl. No. 14/198,104, Response filed Sep. 17, 2015 to Restriction Requirement dated Jul. 17, 2015", 7 pgs.

"U.S. Appl. No. 14/198,104, Restriction Requirement dated Jul. 17, 2015", 5 pgs.

"U.S. Appl. No. 14/271,958, Preliminary Amendment filed Aug. 28, 2014", 3 pgs.

(56) References Cited

OTHER PUBLICATIONS

"U.S. Appl. No. 14/271,958, Restriction Requirement dated Sep. 28, 2015", 6 pgs.
"Application Serial No. PCT/US2014/037128, International Preliminary Report on Patentability dated Nov. 19, 2015", 9 pgs.
"Canadian Application Serial No. 2,827,559, Voluntary Amendment filed Jun. 18, 2014", 18 pgs.
"Chinese Application Serial No. 201280016435.4, Office Action dated Jan. 26, 2015", (w/ English Translation), 17 pgs.
"European Application Serial No. 12748999.5, Extended European Search Report dated Apr. 1, 2015", 8 pgs.
"European Application Serial No. 12748999.5, Response filed Oct. 16, 2015 to Extended European Search Report dated Apr. 1, 2015", 6 pgs.
"International Application Serial No. PCT/US2012/026031, International Preliminary Report on Patentability dated Mar. 27, 2014", 7 pgs.
"International Application Serial No. PCT/US2012/026031, International Search Report dated Jun. 6, 2012", 2 pgs.
"International Application Serial No. PCT/US2012/026031, Written Opinion dated Jun. 6, 2012", 5 pgs.
"International Application Serial No. PCT/US2012/063960, International Preliminary Report on Patentability dated May 22, 2014", 8 pgs.
"International Application Serial No. PCT/US2012/063960, International Search Report dated Jan. 23, 2013", 4 pgs.
"International Application Serial No. PCT/US2012/063960, Written Opinion dated Jan. 23, 2013", 8 pgs.
"International Application Serial No. PCT/US2014/037128, International Search Report dated Aug. 20, 2014", 6 pgs.
"International Application Serial No. PCT/US2014/037128, Written Opinion dated Aug. 20, 2014", 7 pgs.
"Russian Application Serial No. 2013142684, Office Action dated Nov. 28, 2013", 4 pgs.
"Russian Federation Application Serial No. 2013142684, Office Action dated Dec. 4, 2015", (w/ English Translation), 9 pgs.
"Science in Action: Hydraulic Fracturing Research Study", U.S. Environmental Protection Agency (EPA) Office of Research and Development, Document No. EPA/600/F-10/002, (Jun. 2010), 2 pgs.
Brinker, C. J, et al., "Sol-Gel Science: The Physics and Chemistry of Sol-Gel Processing", Pgs. from Chapter 3: Hydrolysis and Condensation II-Silicates, Academic Press, Inc. San Diego, CA, (1990), 99-107.
Dickson, D J, et al., "Photobiological hydrogen production from Synechocystis sp. PCC 6803 encapsulated in silica sol-gel", International Journal of Hydrogen Energy, Elsevier Science Publishers B. V. Banking, GB vol. 34, No. 1, (Jan. 1, 2009), 204-215.
Ferrer, Marla L., et al., "Biocompatible Sol-Gel Route for Encapsulation of Living Bacteria in Organically Modified Silica Matrixes", Chemistry of Materials, 15(19), (2003), 3614-3618.
Fung, W.-Y., et al., "Agrowaste-Based Nanofibers as a Probiotic Encapsulant: Fabrication and Characterization", Journal of Agricultural and Food Chemistry, 59(15), (2011), 8140-8147.
Gensheimer, M., et al., "Novel Biohybrid Materials by Electrospinning: Nanofibers of Poly(ethylene oxide) and Living Bacteria", Advanced Materials, 19, (2007), 2480-2482.
Gensheimer, M., et al., "Polymer/Bacteria Composite Nanofiber Nonwovens by Electrospinning of Living Bacteria Protected by Hydrogel Microparticles", Macromolecular Bioscience, 11(3), (2011), 333-337.
Ho, C, et al., "Enzymatic Properties of Atrazine Chlorohydrolase Entrapped in Biomimetic Silica", Journal of Applied Biological Chemistry, 51(4), (2008), 143-147.
Kandimalla, Vivek B., et al., "Immobilization of Biornolecules in Sol-Gels: Biological and Analytical Applications", Critical Review in Analytical Chemistry, 36(2), (2006), 73-106.
Kauffmann, Carl, et al., "Entrapment of atrazine chlorohydrolase in sol-gel glass matrix", Journal of Biotechnology, 62(3), (1998), 169-176.

Kauffmann, Carl, et al., "Novel Methodology for Enzymatic Removal of Atrazine from Water by CBD-Fusion Protein Immobilized on Cellulose", Environ. Sci. Technol., 34, (2000), 1292-1296.
Kirby, J. R, "Designer bacteria degrades toxin", Nat Chem Biol., 6(6), (Jun. 2010), 398-399.
Klein, S., et al., "Encapsulation of Bacterial Cells in Electrospun Microtubes", Biomacromolecules, 10(7), (2009), 1751-1756.
Klein, S., et al., "Encapsulation of *Pseudomonas* sp. ADP cells in electrospun microtubes for atrazine bioremediation", Journal of Industrial Microbiology & Biotechnology, 39(11), (2012), 1605-1613.
Liu, Y., et al., "Engineering of bio-hybrid materials by electrospinning polymer-microbe fibers", Proc. Natl. Acad. Sci. USA, 106(34), (2009), 14201-14206.
Lopez-Rubio, A., et al., "Electrospinning as a useful technique for the encapsulation of living bifidobacteria in food hydrocolloids", Food Hydrocolloids, 28(1), (2012), 159-167.
Lopez-Rubio, A., et al., "Encapsulation of Living Bifidobacteria in Ultrathin PVOH Electrospun Fibers", Biomacromolecules 10, (2009), 2823-2829.
Ma, T., et al., "Enhancement of atrazine degradation by crude and immobilized enzymes in two agricultural soils", Environ Earth Sci., Online Publication, (2011), 7 pgs.
Ma, Y., et al., "The Research of Immobilized Atrazine Degrading Bacteria Degrading Characteristics", International Conference on Environmental Science and Information Application Technology, 2009. ESIAT 2009, vol. 1, (2009), 677-680.
Macias-Flores, A., et al., "Atrazine biodegradation by a bacterial community immobilized in two types of packed-bed biofilm reactors", World J Microbiol Biotechnol., 25, (2009), 2195-2204.
Mantsch, H. H, et al., "Infrared Spectroscopy of Biomolecules", Chapter 9, Section 9.7.2.1, Wily-Liss, Inc., New York, (1996), p. 266.
Meunier, C F, et al., "Encapsulation of cells within silica matrixes: Towards a new advance in the conception of living hybrid materials", Journal of Colloid and Interface Science, Acadamic Press, New York, NY, US, vol. 342, No. 2, (Feb. 15, 2010), 211-224.
Meunier, Christophe F., et al., "Investigation of different silica precursors: Design of biocompatible silica gels with long term bio-activity of entrapped thylakoids toward artificial leaf", Journal of Materials Chemistry, 19, (2009), 4131-4137.
Mutlu, Baris R., et al., "Silicon alkoxide cross-linked silica nanoparticle gels for encapsulation of bacterial biocatalysts", Journal of Materials Chemistry A, (2013), 10 pgs.
Nedovic, V., et al., "Fundamentals of Cell Immobilization Biotechnology", Adapted from p. 15, Part 1, (2003), 36 pgs.
Patel, Alpa C, et al., "In Situ Encapsulation of Horseradish Peroxidase in Electrospun Porous Silica Fibers for Potential Biosensor Applications", Nano Letters, vol. 6, No. 5, (May 1, 2006), 1042-1046.
Reategui, E., et al., "Encapsulation of Mammalian Cells in Hybrid Inorganic Matrices for Developing Bio-detection Applications", Alley Conference 2010, Poster, (2010), 1 pg.
Reategui, E., et al., "Silica gel-encapsulated AtzA biocatalyst for atrazine biodegradation", Appl Microbiol Biotechnol., [Epub ahead of print], (Jan. 7, 2012), 10 pgs.
Reetz, Manfred T., "Chapter 6—Practical Protocols for Lipase Immobilization", Immobilization of Enzymes and Cells, Second Edition—Edited by Jose M. Guisan, (2006), 65-76.
Riddle, Kathryn W, et al., "Biomaterials for Cell Immobilization: A look at carrier design", Kathryn W. Riddle and David J. Mooney, University of Michigan, Chemical Engineering, (2004), 19 pgs.
Rietti-Shati, M, et al., "Atrazine Degradation by Pseudomonas strain ADP Entrapped in Sol-Gel Glass", Journal of Sol-Gel Science and Technology, vol. 7, No. 1-2, (1996), 77-79.
Rim, N. G., et al., "Current approaches to electrospun nanofibers for tissue engineering", Biomedical Materials, 8(1), (2013), 1-14.
Ruiz-Hitzky, Eduardo, et al., "An Introduction to Bio-nanohybrid Materials", Bio-inorganic Hybrid Nanomaterials, Edited by Eduardo Ruiz-Hitzky, Katsuhiko Ariga and Yuri Lvov, (2008), 1.
Salalha, W., et al., "Encapsulation of bacteria and viruses in electrospun nanofibres", Nanotechnology, 17, (2006), 4675-4681.

(56) References Cited

OTHER PUBLICATIONS

Shona, Pek Y, et al., "A thixotropic nanocomposite gel for three-dimensional cell culture", Nature Nanotechnology vol. 3, No. 11, (Sep. 28, 2008), 671-675.
Siripattanakul, S., et al., "Atrazine removal in agricultural infiltrate by bioaugmented polyvinyl alcohol immobilized and free Agrobacterium radiobacter J14a: A sand column study", Chemosphere, 74, (2009), 308-313.
Srivastava, Y., et al., "Electrospinning of hollow and core/sheath nanofibers using a microfluidic manifold", Microfluidics and Nanofluidics, 4(3), (2007), 245-250.
Tafoya-Garnica, A., et al., "Kinetics of atrazine biodegradation by suspended and immobilized mixed microbial cells cultivated in continuous systems", Journal of Chemical Technology & Biotechnology, 84(7), (Jul. 2009), 982-991.
Vivek, Kandimalla, et al., "Immobilization of Biomolecules in Sol-Gels Biological and Analytical Applications", Critical Reiviews in Analytical Chemistry, vol. 36, No. 2, (Jul. 1, 2006), 73-106.
Wright, J. D, "Sol-Gel Materials: Chemistry and Applications", Chapter 2: Silica Sol-Gels: Reaction Mechanisms, Gordon and Breach Science Publishers, (2001), 15-31.
Yu, M., et al., "RNA sequencing of pancreatic circulating tumour cells implicates WNT signalling in metastasis", Nature, 487(7408), (2012), 510-515.
Zhang, X., et al., "Flexible Generation of Gradient Electrospinning Nanofibers Using a Microfluidic Assisted Approach", Langmuir, 28(26), (2012), 10026-10032.
Zou, et al., "Polymer/Silica Nanocomposites: Preparation, Characterization, Properties, and Applications", Chem. Rev, (2008), 3893-3957.
Zussman, E., "Encapsulation of cells within electrospun fibers", Polymers for Advanced Technologies, 22(3), (2011), 366-371.

\* cited by examiner

SYSTEM AND MEMBRANE FOR WASTEWATER-GENERATED ENERGY AND GAS

PRIORITY CLAIM

This application claims the benefit of U.S. Provisional Patent Application Ser. No. 62/064,183, filed on Oct. 15, 2014, the benefit of priority of which is claimed hereby and which is incorporated by reference herein in its entirety.

CROSS-REFERENCE TO RELATED APPLICATION

This application is related to U.S. Provisional Patent Application No. 62/241,910, filed on Oct. 15, 2015, entitled "MEMBRANES FOR WASTEWATER-GENERATED ENERGY AND GAS," the entire disclosure of which is hereby expressly incorporated by reference herein.

BACKGROUND

Wastewater or sewage treatment is an important process used to remove physical, chemical, or biological contaminants. Typically, an objective of wastewater treatment is to produce an environmentally safe fluid waste stream or a solid waste suitable for disposal or further use. Wastewater treatment methods typically involve multiple steps including, but not limited to, pretreatment, primary treatment, aeration, secondary treatment, and sludge treatment. The multiple processes involved in wastewater treatment can consume a large amount of energy.

Overview

Examples disclosed herein use a multi-layer membrane containing bacteria to extract energy from wastewater. Examples can include a composite membrane including one or more porous layers, wherein at least one of the layers can be configured to convey a gas produced during treatment of a wastewater fluid. Bacteria can be immobilized within the composite membrane, such as within at least one of the layers, wherein the bacteria can produce the gas during treatment of the wastewater. Examples provide increased gas or energy recovery from current wastewater treatment techniques. For example, by immobilizing or encapsulating the bacteria in the composite membrane, concentrations of bacteria can be optimized to produce a desired amount of gas, such as hydrogen. Further, because the bacteria are immobilized, they are protected from harmful influences and competition and can be permitted to grow within the composite membrane or kept in a non-growing state. Examples can include composite membranes having multiple layers or sheets to increase surface area and provide a low resistance path of the gas from the bacteria-containing layers to the gas-filled layers.

Examples can provide a multi-layer membrane having a dry matrix layer sandwiched between one or more additional layers on each side of the dry matrix layer that can contain encapsulated or otherwise immobilized bacteria. The bacteria can be configured to produce a gas from one or more compounds in the wastewater. The dry matrix layer can receive the production gas from the bacteria-containing layers. The dry matrix layer and the bacteria-containing layers can be porous structures, including highly porous structures, such, as, for example, silica gels. Examples can provide one or more components disposed between the dry matrix layer and the bacteria-containing layers, such as, for example, one or more of coatings and adhesive layers.

Examples can provide extraction of various gases during degradation of organic contaminants in a wastewater stream. For example, hydrogen, carbon dioxide, or methane can be extracted and further used either industrially (e.g., carbon dioxide) or to produce useful, clean energy (e.g., hydrogen or methane). Examples of the present disclosure provide the use of various types of bacteria, including, but not limited to, acetogenic and methanogenic bacteria. Advantages of such examples include extracting clean, non-greenhouse gases, such as hydrogen.

Various examples can include a composite membrane used in various stages of a typical wastewater treatment system or during treatment of another organic-rich waste stream such as an industrial, agricultural, or animal waste stream. In an example, the membrane can be placed in a recycle stream of a wastewater treatment system. Recycle streams typically have an increased concentration of organic contaminants, such that the increased levels of contaminants can provide a driving force for the bacteria to produce a useful gas. Further examples include, placing the membrane in a wastewater, industrial, agricultural, or animal waste treatment facility prior to an aeration step, commonly used in facilities today. Such examples can provide the benefit of reducing an amount of energy necessary to aerate the wastewater fluid. For example, the bacteria immobilized within the composite membrane partially break down the organic compounds to produce a useful gas for extraction. Because the energy necessary to aerate a wastewater stream depends on the type and concentration of organic compounds present, the partially broken down compounds can be aerated with expending less energy than complete or non-broken down organic compounds.

Examples can provide extraction of a production gas using a manifold potted to or otherwise in fluid connection with the composite membrane.

BRIEF DESCRIPTION OF THE DRAWINGS

In the drawings, which are not necessarily drawn to scale, illustrate generally, by way of example, but not by way of limitation, various embodiments discussed in the present document.

DETAILED DESCRIPTION

Figure 1A:
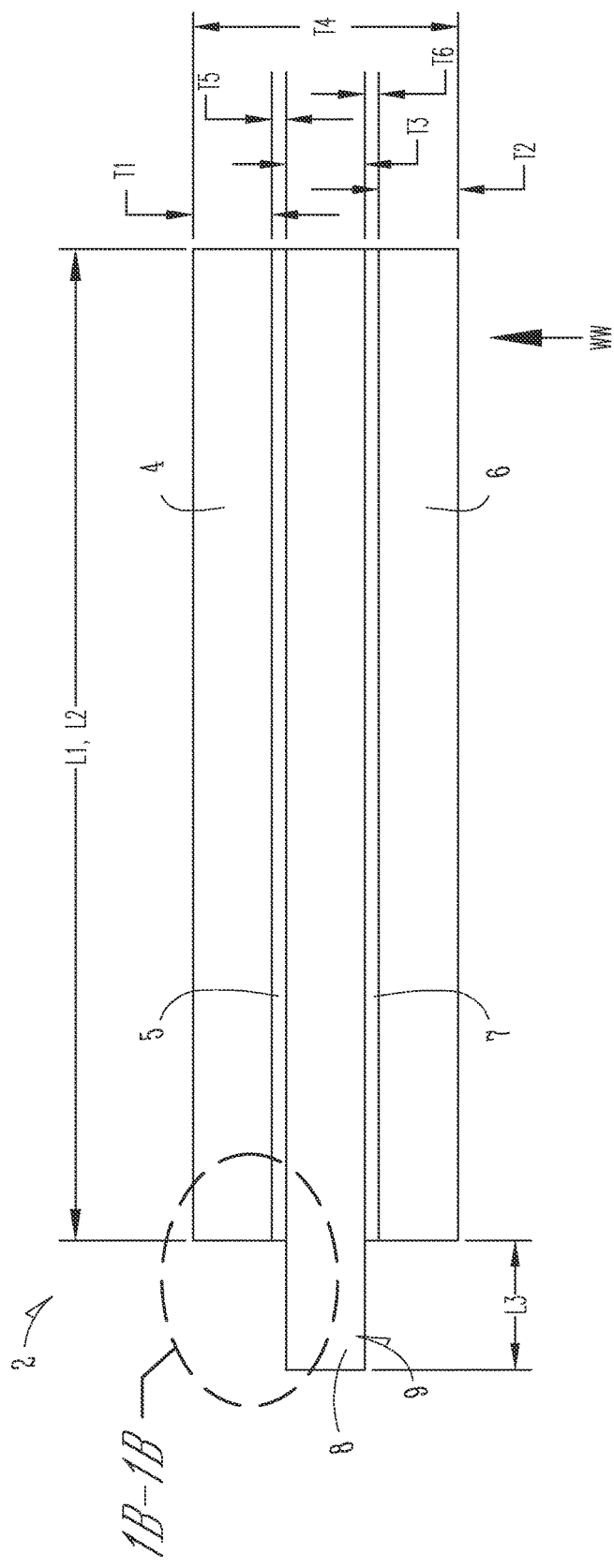
FIG. 1A is a side view of an example composite membrane, in accordance with the present application.

Wastewater, including any water that has been affected by an anthropogenic influence, such as, human waste, animal waste, agricultural waste, washing water, rainfall, industrial waste, highway drainage, among others, is a potential source of energy. However, treating wastewater consumes a substantial amount of energy to reuse or reintroduce the water to the environment. Wastewater contaminants, as described herein, typically are nutrient and energy dense compounds. The present inventors recognize that energy can be extracted from these energy dense compounds. According to the present disclosure, a composite fermentative membrane can be used to extract gas, usable as a source of energy or an industrial product, from wastewater contaminants. The composite fermentative membrane of the present disclosure can use wastewater as an input to generate a clean-burning product, such as hydrogen or methane, or an industrial product, such as carbon dioxide, with less post-processing than current wastewater methods and systems. Examples according to the present disclosure include membranes, systems, and associated methods for extracting or producing a gas from wastewater stream.

The membranes described herein can include multiple layers that together form the composite membrane. In examples, each of the multiple layers can be one or more sheets, or one or more planar or substantially planar layers of material. A dry matrix layer can be used for efficient gas (for example, hydrogen or methane) capture. The dry matrix layer can be sandwiched between one or more additional layers on each side of the dry matrix layer that can contain encapsulated or otherwise immobilized bacteria. The dry matrix layer can receive the gas produced by the bacteria in the bacteria-containing layers. (The dry matrix layer is also referred to herein as a gas-filled layer since it collects the gas produced by the bacteria-containing layers.) The outer bacteria-containing layers surrounding the dry matrix layer can be wettable by the wastewater. The present disclosure includes various examples of composite membranes having a sandwich-like structure of a dry, matrix layer sandwiched between two or more wettable bacteria-containing layers. In the various examples, good connectivity between the dry matrix layer and each of the bacteria-containing layers can provide for good transfer of the produced gas from the bacteria-containing layers to the dry matrix layer.

As described below, in some examples, planar or substantially planar layers that form the composite membrane can be physically separate from one another. In an example, planar or substantially planar layers can be sheets that can be assembled together by stacking the sheets on top of one another and then coupling or connecting the sheets together. In some examples, the layers of sheets can be formed by depositing layers on top of one another. In yet other examples, the layers can be formed from a common block of a starting material with different regions of the block being functionalized or otherwise modified to form the wettable outer layers and the dry inner layer, such that the layers of the composite membrane may have never been physically separate from one another. As used herein, the term "layer," when referring to the dry matrix layer (or gas-filled layer) and the bacteria-containing layers of the composite membrane, can refer to sheets that are originally separate and then connected or coupled to form one or more layers in a multi-sheet composite membrane. The term "layer," as used herein when referring to the dry matrix layer and the bacteria-containing layers of the composite membrane, can refer to one or more layers or regions in a common structure, e.g., a block of starting material, that were not physically separate from one or more other layers or regions of the composite membrane, but that have been modified or functionalized so that adjacent "layers" have distinct physical or chemical properties or abilities.

Figure 1B:
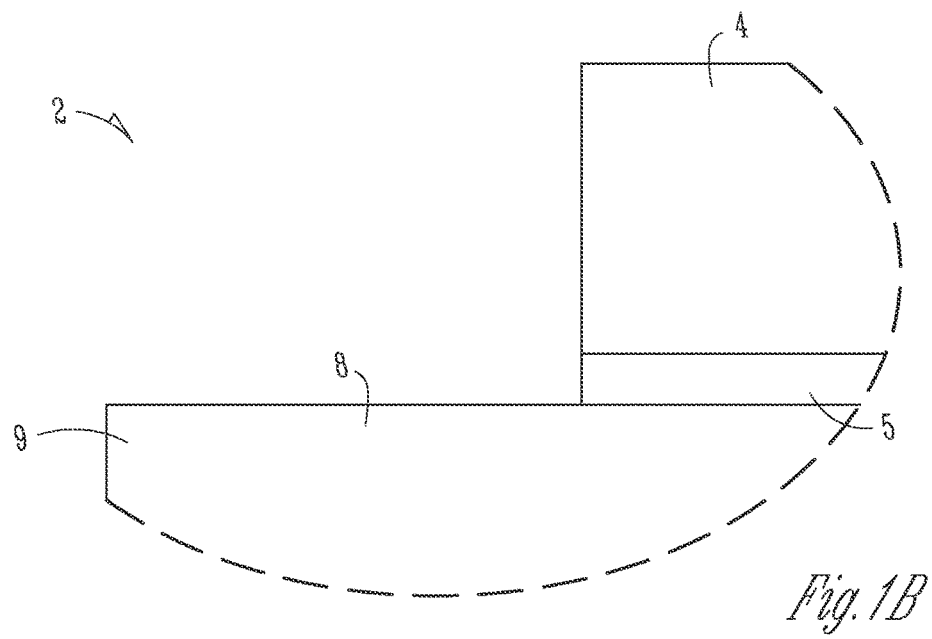
FIG. 1B is an enlarged view of a portion of the composite membrane in FIG. 1A.

FIGS. 1A and 1B illustrate an example of a composite membrane 2, according to the present disclosure. FIG. 1A is a side view of the composite membrane 2, and FIG. 1B is an enlarged view of a portion of FIG. 1A taken at 1B-1B.

In various examples, the composite membrane 2 can immobilize bacteria and facilitates gas collection, so as to provide increased gas production from waste, such as organic compounds in wastewater, and reliable scale-up. Although production of various types of gases is contemplated, such as a clean-burning product, e.g., hydrogen or methane, or an industrial product, such as carbon monoxide, the present disclosure generally refers to production of hydrogen.

The composite membrane 2 can be generally referred to herein as a sandwich structure, e.g., as a composite of at least one inner layer disposed between two or more outer layers. In an example, the composite membrane 2 can include a first layer 4 of a first material. The first layer 4 can include a first immobilized bacteria, wherein the first immobilized bacteria can be configured to produce a first gas from one or more compounds in a wastewater fluid. The composite membrane 2 can include a second layer 6 of a second material. The second layer can include a second immobilized bacteria or material, wherein the second immobilized bacteria can be configured to produce a second gas from one or more compounds in the wastewater. The second layer 6 can be disposed below the first layer 4. In an example, the first layer 4 and the second 6 layer can each be planar or substantially planar.

As shown in FIG. 1A, a third layer 8 of a third material can be at least partially disposed between the first layer 4 and the second layer 6. In an example, the third layer 8 can be planar or substantially planar. The third layer 8 can be configured to receive at least one of the first gas and the second gas as it is produced by the reactions between the immobilized bacteria and the wastewater. The gas can include but is not limited to hydrogen, carbon dioxide, methane, or combinations thereof.

In an example, the first layer 4 and second layer 6 can have a length substantially the same or different. In various examples, one or both of a length L1 of the first layer 4 and a length L2 of the second layer 6 can be from about 0.5 meters to about 2 meters or more. In an example, the length L1 and L2 can be about 1.0 meter. In an example, the first layer 4 and the second layer 6 can have a thickness substantially the same or different. In various examples, one or both of a thickness T1 of the first layer 4 and a thickness T2 of the second layer 6 can be from about 0.1 millimeter to about 1 centimeter. In other examples, one or both of the thicknesses T1 and T2 can be from about 10 microns to about 1 millimeter. In other examples, one or both of the thicknesses T1 and T2 can be from about 5 microns to about 10 microns. A thickness T3 of the third layer 8 can depend, in part, on one or both of the thicknesses T1 and T2. In an example, the thickness T3 can be greater than each of the thicknesses T1 or T2. In an example, the thickness T3 can be about equal to a combined thickness of T1 and T2. In various examples, the thickness T3 can be from about 0.25 centimeters to about 2 centimeters. In other examples, the thickness T3 can be from about 10 microns to about 2 millimeters. In other examples, the thickness T3 can be from about 10 microns to about 30 microns. In an example, the composite membrane 2 can have a total thickness T4 of about 0.2 millimeters to about 3 centimeters. Depending on a thickness of each of the layers 4, 6 and 8 (and any additional components of the composite membrane as described below), the total thickness T4 can be less than about 0.2 millimeters or more than about 3 centimeters.

Figure 6:
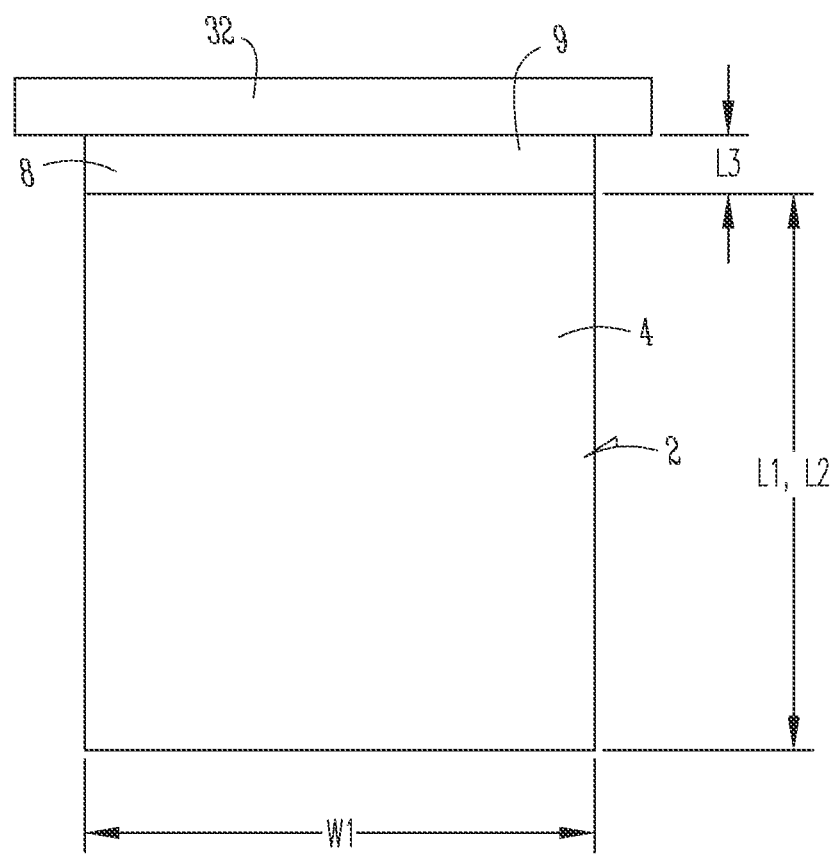
FIG. 6 is a top view of an example system including a composite membrane and potted manifold, in accordance with the present application.

In an example, the third layer 8 can include an extended portion 9. The extended portion 9 can be configured to be potted to a first manifold, such as a vacuum manifold. As used herein, the terms "potted," "potting," or their equivalent, can include coupling the extended portion 9 to the first manifold so that the third layer 8 is in fluid communication with the first manifold, e.g., so that the production gas can be extracted from the third layer 8 into the manifold. Examples of potting can include, but are not limited to, at least one of a compression fitting, such as a snap fit or press fit, adhering, such as with an adhesive or a sealant, and any other technique used to connect the third layer with a first manifold, e.g., as shown in FIG. 6, such that the third layer 8 can be in fluid communication with the first manifold. In an example, the extended portion 9 can have a length L3 from about 8 millimeters to about 35 millimeters.

In various examples, the first layer 4 and second layer 6 can include a polymer, a copolymer, a block copolymer matrix, silica, or combinations thereof, including, but not limited to poly(vinyl alcohol), polyacrylamide, poly(ethylene oxide), polypropylene oxide, latex, nylon, Pluronic F127 dimethacrylate, tetramethyl orthosilicate (TMOS), tetramethylorthosilicate (TEOS), tetrakis(2-hydroxyethyl) orthosilicate (THEOS) or a silica gel made out of any other silica precursor with hydrolysable sidegroups or combinations thereof. In an example, the first material of the first layer 4 can be the same material or a different material as the second material of the second layer 6.

In various examples, bacteria are immobilized in the first layer 4 and the second layer 6. The polymer, copolymer, silica gel or block copolymer of the first and second layers 4, 6 can contain an immobilized or encapsulated bacteria, such as one or more acetogenic bacteria or methanogenic bacteria. Such a design, for example, can facilitate the use of pure cultures of acetogens, chosen for their hydrogen producing capabilities, as well as engineered hydrogen-producing communities or genetically engineered organisms capable of hydrogen production. In an example, the first immobilized bacteria of the first layer 4 are the same or different than the second immobilized bacteria of the second layer 6. In an example, the first or second immobilized bacteria can be encapsulated in the first or second material, such as in a silica-matrix. The first layer 4 and the second layer 6 can be filled with the bacteria and can be strong and stiff. In an example, the first layer 4 or the second layer 6 can be a silica gel with a porous structure, and in some examples, the first layer 4 and the second layer 6 can be highly porous. In an example wherein one or both of the first layer 4 and the second layer 6 comprise a silica-based material, such as a silica gel, the first layer 4 and the second layer 6 can be formed by known production methods including, but not limited to, electro spinning, freeze-casting, and molding.

In an example, the immobilized or encapsulated bacteria includes acetogenic bacteria, which produce hydrogen via the fermentation of carbohydrates, and other wastewater organic materials. In anaerobic environments, however, hydrogen generated by acetogenic bacteria is quickly consumed by methanogenic bacteria, producing methane. It is the consumption of the hydrogen that allows acetogenesis to occur, as this hydrogen-producing reaction is not thermodynamically favorable at high hydrogen partial pressures. Enriched or isolated acetogenic bacteria in combination with a method of efficiently removing hydrogen, permits these organisms to be used to generate hydrogen from the fermentable compounds found in wastewater. The biochemically-derived hydrogen from wastewater is a "free" substrate and the fermentation is anaerobic, resulting in no real cost for biohydrogen production other than the capture of the product. In various examples, the immobilized bacteria include methanogenic bacteria.

In an example, free and immobilized cells of *C. butyricum* are used for their ability to generate hydrogen via the fermentation of hexoses, including glucose. Municipal wastewater, however, is a complex mixture of compounds, including organic acids. Therefore, the use of a mixed enrichment of organisms from wastewater solids that produce hydrogen and are capable of using additional components of the waste stream for hydrogen production is contemplated. Immobilization of other combinations of hydrogen-, methane-, and carbon dioxide-producing bacteria are also contemplated, such as pure or mixed cultures of acetoclastic methanogens.

The composite membrane 2 can use the diffusive transport of carbon and energy sources to the immobilized acetogenic bacteria and the diffusive transport of hydrogen away from the cell surface and into the third layer 8, as discussed herein. A combination of reaction-diffusion equations (Equation 1 below), paired with hydrogen production rates, r, is used to describe concentration profiles, C, of substrate and hydrogen in the composite fermentative membrane as a function of depth, x, and time, t.

$$\frac{\partial C}{\partial t} = \frac{\partial^2 C}{\partial x^2} \pm r \qquad (1)$$

In an example, the composite membrane 2 can be designed to control chemical diffusion and to maintain pure or mixed culture viability and/or activity. Further, as described herein, membrane behavior can be understood mathematically, so as to effectively model the transport of reactants and products through the membranes to predict and optimize performance.

Polyacrylamide has been shown to immobilize bacteria, such as *Burkholderia xenovorans* strain LB400, and preserve their activity for at least 10 months; *Burkholderia xenovorans* strain LB400 is an aerobic PCB-degrading bacterium. Other types of bacteria, such as methanogens or acetogens, can be immobilized in the polymer, as described herein. A benefit of the polymer matrix configuration of the composite membrane, as described in the present disclosure, includes providing diffusion limitations that can be used to promote the capture of the hydrogen produced therein. Dissolution and diffusion of wastewater compounds in the dense polymer/matrix structure provides a constant stream of carbon and nutrients for consumption by the immobilized bacteria. Other polymers, for example, a polymer, copolymer, and/or block copolymer matrices, including, but not limited to poly(vinyl alcohol), polyacrylamide, poly(ethylene oxide), polypropylene oxide, latex, nylon, Pluronic F127 dimethacrylate, tetramethyl orthosilicate (TMOS), Tetramethylorthosilicate (TEOS), Tetrakis(2-hydroxyethyl) orthosilicate (THEOS) or a silica gel made out of any other silica precursor with hydrolysable sidegroups or combinations thereof, are used to immobilize the bacteria and preserve their activity, in various examples.

In various examples, the third layer 8 can include a polymer, a copolymer, a block copolymer matrix, or combinations thereof, including, but not limited to poly(vinyl alcohol), polyacrylamide, poly(ethylene oxide), polypropylene oxide, latex, nylon, Pluronic F127 dimethacrylate, tetramethyl orthosilicate (TMOS), Tetramethylorthosilicate (TEOS), Tetrakis(2-hydroxyethyl)orthosilicate (THEOS) or a silica gel made out of any other silica precursor with hydrolysable sidegroups or combinations thereof. In an example, the third layer 8 can comprise the same base material or a different base material as the first layer 4 or the second layer 6. In an example, the third layer 8 can be the same base material as the first layer 4 and the second layer 6, but substantially or completely abiotic (e.g., it does not contain an immobilized bacteria).

In an example, the third layer 8 can be stiff and can be comparable to a strong sponge. In an example, the third layer 8 can be a porous structure. In an example, the third layer 8 can be a highly porous structure. In an example, the third layer 8 can comprise a plurality of pores that can be of varying size, orientation, and placement. In an example, the third layer 8 can be porous or highly porous, but with the pores not generally forming continuous linear channels that extend from one end of the layer 8 to an opposing end of the layer 8, while still permitting the transfer of the production gas into the third layer 8 (from the first layer 4 and the second layer 6), and through the third layer 8 for extraction of the gas. In an example, the third layer 8 can be a silica gel. In an example, a silica gel-based third layer 8 can be formed by known production methods including, but not limited to, freeze-casting, electro spinning or molding.

The first layer 4 and the second layer 6 can be wettable by the wastewater. This can enable good contact between the compounds in the wastewater, which can be converted to the production gas, and the encapsulated bacteria in the first layer 4 and the second layer 6. The bacteria can thus generate gas, such as one or more of hydrogen, methane, and carbon monoxide. The third layer 8 can be dry such that the gas can be collected by the third layer 8 and then removed from the membrane 2. As described further below, the composite membranes disclosed herein can be configured in various ways to keep the third layer 8 dry and the first and second layers 4 and 6 wettable. As used herein, the term "dry" with reference to the third layer 8 can mean that the layer 8 is substantially free from water.

In some examples, the first layer 4 can be in direct contact with the third layer 8 and the second layer 6 can be in direct contact with the third layer 8. In some examples, components, such as 5 and 7 shown in FIG. 1A, can be disposed between the first layer 4 and the third layer 8 and between the second layer 6 and the third layer 8. These components can provide material properties, such as adhesion or hydrophobicity, as described below. The composite membrane 2 can be configured such that sufficient contact can be provided between the first layer 4 and the third layer 8 and between the second layer 6 and the third layer 8, in part to allow for diffusion of the gas from the first layer 4 and the second layer 6 to the third layer 8.

In an example, the composite membrane 2 can include a hydrophobic coating 5, 7 over at least a portion of the third layer 8. For example, the hydrophobic coating 5 can be disposed between the first layer 4 and the third layer 8, and the hydrophobic coating 7 can be disposed between the second layer 6 and the third layer 8, such that the third layer 8 does not contact the first layer 4 or the second layer 6. The hydrophobic coatings 5, 7 can be configured to prevent water from passing into the third layer 8, but substantially allow the produced gas to pass into the third layer 8. As such, the coatings 5 and 7 can help keep the third layer 8 dry, while allowing the first layer 4 and the second layer 6 to be wetted by the wastewater. As described herein with reference to FIGS. 6-9, a manifold system can be used to increase the gas yield and efficiency of the third layer 8.

The hydrophobic coatings 5, 7 can be in close contact with the acetogens that produce the hydrogen, consequently substantially enhancing the efficiency of hydrogen collection. Different types of coatings 5, 7 can be used, each with respective efficiency in collecting hydrogen from the fermentative membranes (e.g., first and second layers 4, 6). Two examples of materials for the hydrophobic coatings 5, 7 can include, but are not limited to, hyper-porous silica and microporous polyethylene. Silica-based matrices can have tunable porosity, can be thermally and mechanical stable, can be chemically inert, and can be resistant to microbial attack. Furthermore, silica-gel encapsulation methods can be carried out under mild conditions via the aqueous sol-gel process, minimizing cell and enzyme damage during encapsulation. Combinations of hyper-porous silica and microporous polyethylene compositions are contemplated for the coatings 5, 7. The coatings 5,7 can be disposed on the surface of the layers 4, 6 or 8 using known surface treatment methods, including, but not limited to, vapor deposition or a solvent-based deposition (e.g., using hexane as a solvent).

Hydrogen production and collection efficiencies can be improved or optimized through manipulation of the composite fermentative membrane module configuration. Examples of module configurations are shown in FIGS. 6-9. A thickness of the coatings 5, 7 can be varied so as to increase efficiency of the gas diffusing into the third layer 8 or increase quality of the produced gas collected.

In some examples, a thickness T5 of the coating 5 or a thickness T6 of the coating 7 can be very thin, e.g., in the angstrom to nanometer range. In an example, the thickness T5 or T6 can be thinner at an interface between the first layer 4 or an interface of the second layer 6, relative to a thickness of the coating not in contact with the first or second layer 4, 6 (e.g., on the sides of the composite membrane 2). Such an example provides the benefit of allowing easier diffusion of the gas from the first layer or second layer 4, 6 into the third layer 8. In an example, the hydrophobic coatings 5, 7 can have a uniform thickness such that T5 and T6 can be substantially the same.

The composite membrane 2 can be contacted with the wastewater such as flowing wastewater or in a reservoir tank, as described herein. Arrow WW generally indicates where the wastewater contacts the composite membrane 2.

A sandwich configuration can increase the area of influence of the third layer 8, improving gas collection and reducing diffusion of the production gas toward the wastewater solution where it would be lost. Many variations on sandwich or layered configurations are contemplated to increase gas production and capture.

In a sandwich configuration, the resistance for diffusion can be reduced by increasing surface area and decreasing thickness of the layers that form the composite membrane. The bacteria-containing layers 4 and 6 can surround the gas-collecting or gas-filled layer 8, enabling efficient collection of the gas by the layer 8 as the gas is produced by the bacteria in the layers 4 and 6. Efficient collection of the gas by the layer 8 can help in increasing production by the bacteria in the layers 4 and 6. In an example having planar or substantially planar layers, a multi-layered configuration can facilitate separate hydrophobic and hydrophilic layers or portions of the membrane, as described below.

A membrane formed of multiple layers can be easy to manufacture at any scale. As described herein, a modular design, such as a composite membrane rack fitted with a gas collection manifold, can enable use of a system with a plurality of composite membranes 2 at any scale. Further purification and concentration of the hydrogen can be accomplished with typical systems commercially available—including municipal sanitary waste, wastewater sludge, and agricultural and industrial waste. The system can operate for long period of time and provide improved wastewater treatment coupled with fuel generation. The system can reduce the need for aeration during wastewater treatment and thus decrease energy usage.

Figure 2:
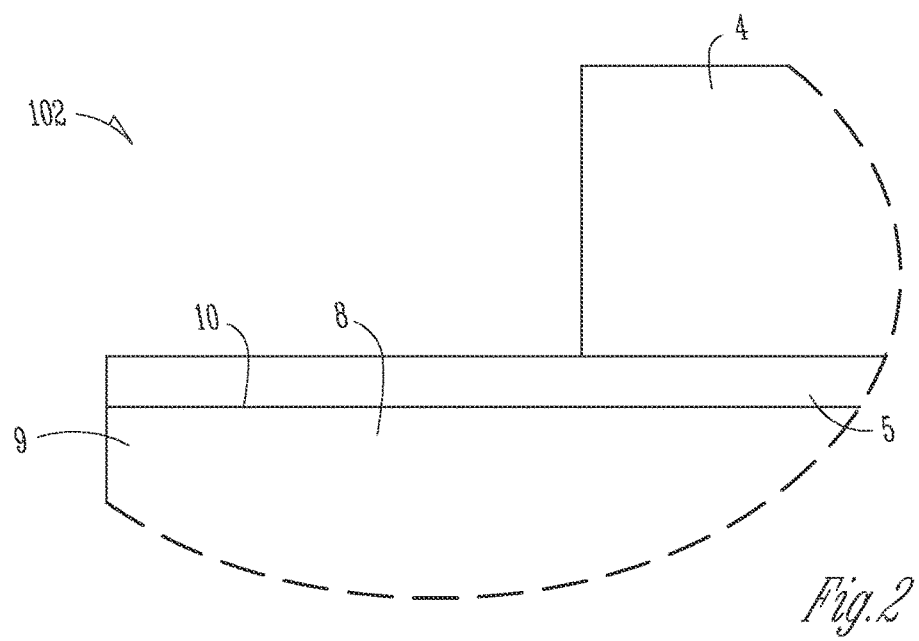
FIG. 2 is a side view of a portion of an example composite membrane, in accordance with the present application.

As shown in FIGS. 1A and 1B, the extended portion 9 can be exposed and not covered by the coating 5 or 7. FIG. 2 illustrates an example of a composite membrane 102 that is similar to the composite membrane 2 of FIGS. 1A and 1B, but a superior side 10 of the extended portion 9 of the third layer 8 can be covered with the hydrophobic coating 5. It is recognized that the opposing inferior side of the extended portion 9 of the third layer 8 can be covered with the hydrophobic coating 7. Since the extended portion 9 can be exposed to the wastewater, it can be advantageous, in an example, to cover the inferior or superior sides of the extended portion 9 of the third layer 8 with the coatings 5 or 7.

Instead of or in addition to the hydrophobic coatings 5, 7, a composite membrane can include one or both of an adhesive interface between the first layer 4 and the third layer 8, and an adhesive interface between the second layer 6 and the third layer 8. In an example, the layers 5 and 7 shown in FIG. 1A can be configured as an adhesive interface in addition to or as an alternative to a hydrophobic coating. In such an example, the layers 5, 7 can be formed of the same or a different material than the materials described above for the hydrophobic coatings. Depending on the material(s) selected, the layers 5 or 7 can function as a hydrophobic adhesive interface. As such, the properties of a hydrophobic coating and an adhesive interface can both be achieved in a single layer between the layers 4 and 8 and between the layers 6 and 8.

In an example, the adhesive interface can be provided in the composite membranes described herein to promote adhesion between one or more first structures and one or more other components of the system. In an example, the composite membrane 2 can include a first adhesive interface that is at least partially disposed between the third layer 8 and the first layer 4. The composite membrane 2 can include a second adhesive interface that is at least partially disposed between the third layer 8 and the second layer 6. As mentioned above, an adhesive interface can provide for improved adhesion between the third layer 8 and at least one of the first layer 4 and the second layer 6. In an example, the third layer 8 that is configured for extraction of the produced gas can be a hydrophobic material and the adhesive interface can provide for adhesion between the hydrophilic material of the bacteria-containing layers 4, 6 and the hydrophobic material of the dry matrix or gas-filled third layer 8.

Figure 3:
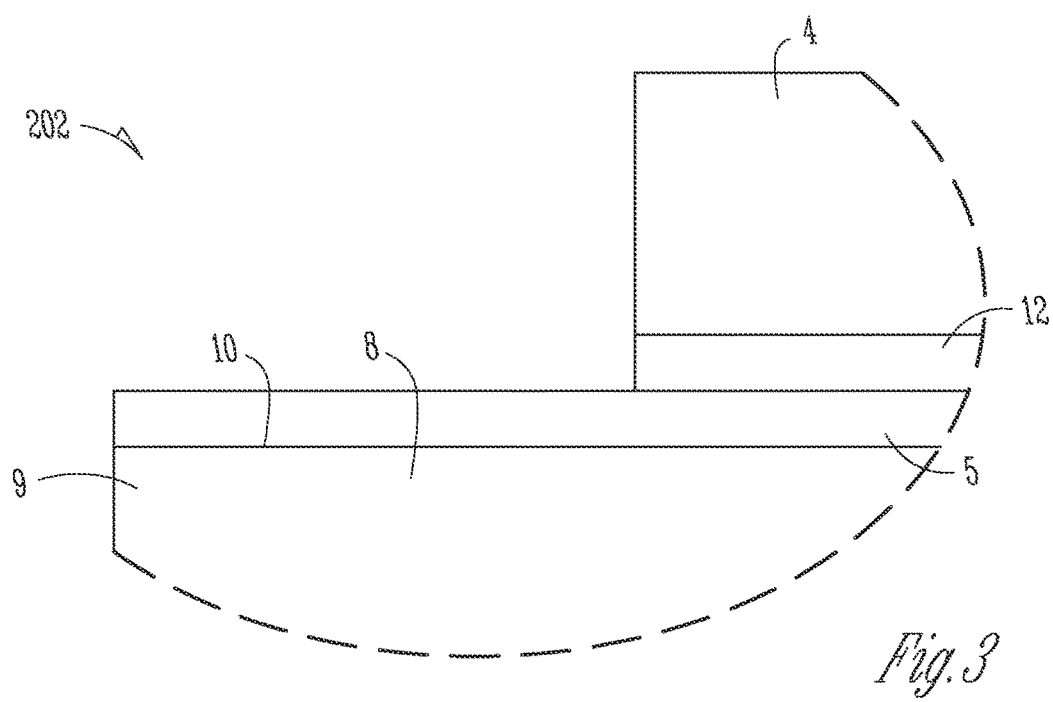
FIG. 3 is a side view of a portion of an example composite membrane, in accordance with the present application.

In an example, each adhesive interface can comprise an adhesive layer applied between at least a portion of the third layer 8 and at least one of the first layer 4 and the second layer 6. As described above, the layers 5, 7 of FIG. 1A can be an adhesive layer, a coating layer or both. As shown in FIG. 3, separate coating and adhesive layers can be provided (see adhesive layer 12).

Examples of adhesive materials that can be used to form the adhesive layer of the adhesive interface can include, but are not limited to, biocompatible adhesives, such as biocompatible wet adhesives (also referred to as biocompatible waterproof or water resistant adhesives), for example a polydopamine adhesive material. Other examples of adhesive material that can be used to form the adhesive interfaces include, but are not limited to, positively-charged polyelectrolytes, such as poly-L-lysine or polyethyleneimine. If a positively charged polyelectrolyte is used as the adhesive material, then the material of one or more of the layers 4, 6, 8 can be negatively charged to allow for adhesion.

A first adhesive interface (see, for example, the layer 5 of FIG. 1A or the layer 12 of FIG. 3) can comprise a portion of at least one of the first layer 4 and the third layer 8 that is chemically modified to improve adhesion between the third layer 8 and the first layer 4. A second adhesive interface (see, for example, the layer 7 of FIG. 1A) can comprise a portion of at least one of the second layer 6 and the third layer 8 that is chemically modified to improve adhesion between the third layer 8 and the second layer 6. The chemical modification of one or more of the layers 4, 6, 8 can include a surface treatment to form an adhesive surface portion of the layer 4, 6, 8 being chemically modified. Examples of chemical modification include, but are not limited to, modification of a hydrophilic material with one or more hydrophobic moieties, modification of a hydrophobic material with one or more hydrophilic moieties, or modification of the material of the layer 4, 6, 8 with a chemical moiety having an adhesion property. Each adhesive interface can provide an adhesion force (e.g., the force that the adhesive interface can withstand before the third layer 8 and the first layer 2 or the second layer 4 are separated). In an example, the adhesion force between the third layer 8 and one of the first and second layers 4, 6 can be at least as large as the shear force of the wastewater fluid on the wetted surfaces of the composite membrane 2.

Reference is made to U.S. Provisional Patent Application No. 62/241,910, filed on Oct. 15, 2015, entitled "MEMBRANES FOR WASTEWATER-GENERATED ENERGY AND GAS," the entire disclosure of which is hereby expressly incorporated by reference herein, which discloses adhesive interfaces for inclusion in the composite membranes described herein.

In an example, the layers 5 or 7 can function as an adhesive-interface and the bacteria can be immobilized in or on the adhesive layers 5 or 7 as an alternative to immobilizing the bacteria in the layers 4 and 6 as described above in reference to the membrane 2 of FIGS. 1A and 1B. This is described further below in reference to FIGS. 10A and 10B.

FIG. 3 illustrates an example of a composite membrane 202 that can include separate layers for an adhesive interface and a hydrophobic coating. In an example, as shown in FIG. 3, the hydrophobic coating 5 can be disposed between the third layer 8 and the first layer 4, and cover the extended portion 9; and an adhesive layer 12 can be disposed between the hydrophobic coating 5 and the first layer 4. It is recognized that a similar construction of a hydrophobic coating and an adhesive layer can be disposed between the third layer 8 and the second layer 6. In an example, the adhesive layer 12 and the hydrophobic coating 5 can be reversed such that the adhesive layer 12 can be disposed between the third layer 8 and the first layer 4, and the hydrophobic coating 5 can be disposed between the adhesive layer 12 and the first layer 4.

As described above, the membrane 2 of FIGS. 1A and 1B can effectively produce a gas from wastewater since the first layer 4 and the second layer 6 can be wettable (and thus hydrophilic), and the third layer 8 can be dry. In the example composite membranes shown in FIGS. 1A-3, the coating 5, 7 can function to keep the third layer 8 dry such that the gas diffuses from the layer 4 or 6 to the third layer 8, but the water does not pass to the third layer 8. The third layer 8 can be formed of the same base material as the layer 4 or 6, in an example, if a hydrophobic coating covers at least a portion of the third layer 8.

Figure 4:
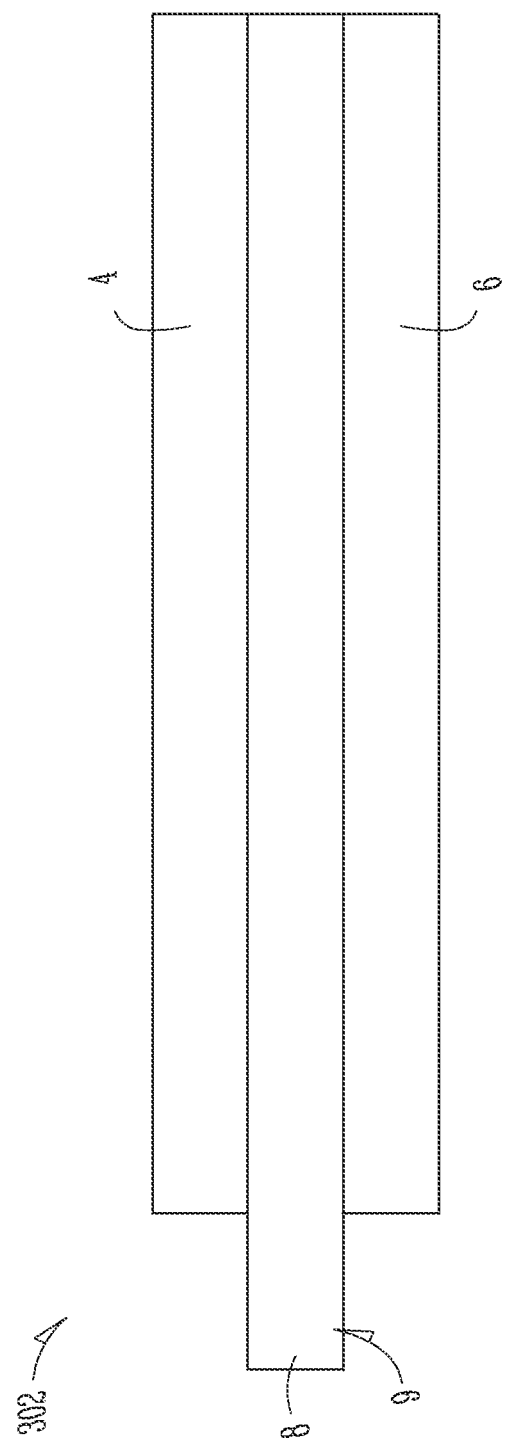
FIG. 4 is a side view of an example composite membrane, in accordance with the present application.

FIG. 4 illustrates an example of a composite membrane 302 which, similar to the membrane 2 of FIGS. 1A and 1B, can include layers 4, 6 and 8, but can exclude the hydrophobic coatings 5 and 7. In an example, the third layer 8 can comprise the same base material or a different base material as the third layer 4 or the second layer 6. In an example, because a hydrophobic coating over the third layer 8 is excluded in the membrane 302, other methods can be used to keep the third layer 8 dry, such as by making at least a portion of the third layer 8 hydrophobic, while allowing the layers 4 and 6 to be wettable, such as by making at least a portion of the layers 4 and 6 hydrophilic (or forming the layers 4 and 6 to be hydrophilic). These other methods can include, but are not limited to, altering, modifying, or functionalizing the selected materials.

As used herein, the term "functionalizing" can include, but is not limited to, adding materials to the base material, such as adding chemical groups to bond to the base material to achieve desired properties, such as, for example, hydrophobicity or hydrophilicity. Functionalizing can include altering or modifying a surface of the material, such as a surface of the layers 4, 6 or 8, by bonding another chemical to the surface of the material, including, but not limited to, covalent bonding. Functionalizing can include modifying all or a portion of the layer, such as modifying an interior region of the layer by, for example, adding another chemical to the interior pores of the layer. Functionalization of the composite membranes described herein can be performed using known techniques. In an example, one or more chemicals, including, but not limited to, trimethylchlorosilane (TMCS) and hexamethyldisilazane (HMDZ or HMDS), can be added to a silica gel to make at least a portion of the gel hydrophobic.

In an example, the third layer 8 can be formed of a different material than the layer 4 or 6. In an example, the third layer 8 can be formed of the same material as the layer 4 or 6, but the third layer 8 can be functionalized to have different material or chemical properties than the layer 4 or 6. In an example, the third layer 8 can be formed of the same material as the layer 4 or 6, and one or both of the layers 4 and 6 can be functionalized to have different material or chemical properties than the layer 8. In an example, the first, second, and third layers 4, 6, and 8 can be generally hydrophilic, such as a porous silica gel, and the third layer 8 can be functionalized to be hydrophobic. In an example, a common block of starting material can be used to form layers 4, 6, and 8, as described below, e.g., by functionalizing different regions of the common block of material according to desired properties for a particular region.

Figure 5:
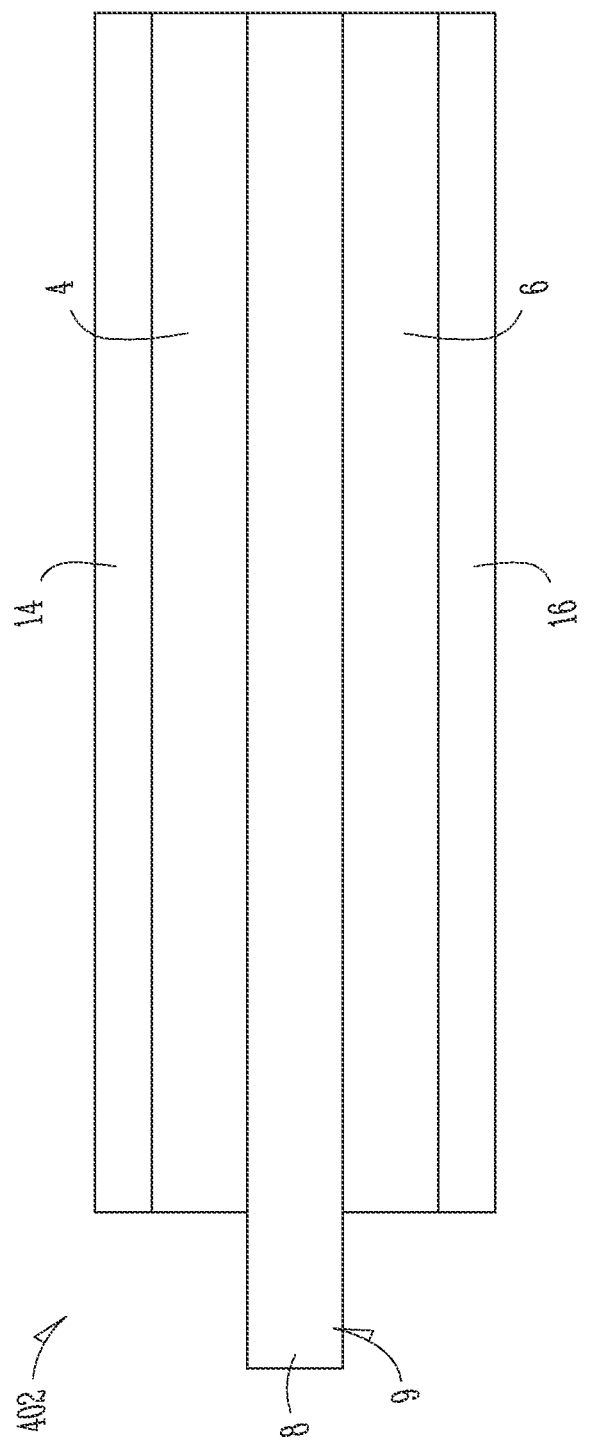
FIG. 5 is a side view of an example composite membrane, in accordance with the present application.

FIG. 5 illustrates an example of a composite membrane 402 that is similar to the membrane 302 of FIG. 4, but can also include additional outer layers. A first outer layer 14 can be disposed on an outer surface of the first layer 4 and a second outer layer 16 can be disposed on an outer surface of the second layer 6. It is recognized that, in an example, a composite membrane could include only one of the first outer layer 14 or the second outer layer 16.

The first outer layer 14 or the second outer layer 16 can be used in the composite membrane 402 to increase diffusion resistance of the gas out of the membrane 402. This increased resistance can facilitate transfer of the gas from the first and second layers 4 and 6 into the third layer 8 by providing comparatively less resistance to the gas flowing from the layers 4 and 6 into the third layer 8, compared to from layers 4 and 6 into the outer layers 14 and 16.

One or both of the first outer layer 14 and the second outer layer 16 can be the same material as layers 4 or 6 or a different material. The first outer layer 14 and the second outer layer 16 can exclude the immobilized bacteria contained in the first layer 4 and the second layer 6. In some examples, one or both of the first outer layer 14 and the second outer layer 16 can be formed of a hydrophilic material such that one or both of the first outer layer 14 and the second outer layer 16 can also be wettable by the wastewater. One or both of the outer layers 14 and 16 can be thinner than the first and second bacteria-containing layers 4 and 6, or one or both of the outer layers 14 and 16 can have a thickness approximately equal to a thickness of the first and second bacteria-containing layers 4 and 6.

FIGS. 1A-5 illustrate various examples of composite membranes having multi-layer designs with different layers and configurations. It is recognized that the various layers can be assembled together in numerous ways to form a composite membrane. In an example, the layers 4, 6 and 8 can be individually formed as sheets and can be separate from one another prior to assembly of the composite membrane. In an example, the separate sheet layers 4, 6 and 8 can be stacked together, or otherwise disposed in a layered assembly, in order to form the composite membranes. In an example, once all the sheet layers of the composite membrane are in a stacked configuration, additional steps can be taken to ensure a dry matrix layer is connected to one or more of the bacteria-containing layers with minimal space between the dry matrix layer and the one or more bacteria-containing layers. As described herein, sufficient contact or connectivity between the dry matrix layer and the bacteria-containing layers can facilitate and improve diffusion of the produced gas from the bacteria-containing layers to the gas-collecting or gas-filled dry matrix layers. In an example, the layers can be compressed together after being stacked together. In an example, a mechanical sieve can apply constant pressure to the layers, such as at the edges, to keep them together during assembly. In an example, grips can be used to press the layers together. In an example, a heat-shrunk plastic frame can be used.

As described above, in some examples, the layers 4, 6 and 8 can include adhesive interface layers or coating layers disposed between the dry matrix layer 8 and the outer bacteria-containing layers 4 and 6. These coatings and adhesive layers can be deposited, or otherwise disposed onto one or more of the layers 4, 6, and 8 using known techniques, including, but not limited to, vapor deposition, solvent-based deposition, extrusion, spin casting, spraying, roll coating, dip coating, and three-dimensional printing.

In an example, layer forming or layer deposition can be used to build or assemble layers of a composite membrane by depositing material of a layer onto one or more already existing layers to form one or more additional layers. In an example, three-dimensional printing can be used to form one or more layers of the composite membranes. In an example, spin coating can be used to form one or more layers of the composite membranes. In an example, a first layer can be formed by depositing a first material, e.g., onto a substrate, and then a second layer of a second material, which can have a composition that is the same or different from the first material, can be deposited onto the first layer. In an example in which a gel is deposited, a composition of the gel can be changed slightly for the second layer. In an example, the second material that will form the second layer can be deposited onto the first layer before the first material that will form the first layer fully cures such that contact and adhesion between the uncured or partially cured first and second materials can be achieved, resulting in adhered and potentially at least partially intermixed first and second layers. In some examples, a transition between adjacent layers can be gradual.

Referring to the composite membrane 302 of FIG. 4, in an example, one or more of the layers 4, 6 and 8 can be printed. In an example, the second layer 6 can be printed, e.g., onto a substrate, then the third layer 8 (which can have different material properties than the second layer 6) can be printed onto the second layer 6, and then the first layer 4 (which can have different material properties than the third layer 8) can be printed on the third layer 8. Referring to the composite membrane 2 of FIG. 1A, in an example, one or more of the layers 4, 6 and 8 can be printed and an adhesive or coating, such as one or both of the coatings 5, 7 (which could additionally or alternatively include an adhesive), can be laid down or deposited in between the printing of the layers 4, 6, and 8.

In an example, some layers of the composite membrane can be printed onto other layers that are not printed, but are otherwise formed using known techniques. The materials for each layer, each adhesive, or each coating can be selected such that the material being deposited or added onto an existing layer can bond sufficiently to the existing layer. Known layer deposition techniques can be used to control thickness and uniform placement, including, but not limited to, vapor deposition and solvent-based deposition techniques.

In an example, the composite membrane can be formed by starting with a single block of material and modifying regions of the block of a starting material to form one or more of the layers of the membrane. A region of the block corresponding to one of the layers of the composite membrane can be functionalized according to the desired properties for the corresponding layer. In an example, a monolithic block of a silica aerogel with a porous structure can be used as a starting material. Outer regions of the monolithic block can be modified or functionalized to provide the desired property or properties of what can become the outer bacteria-containing layers of the composite membrane, e.g., by functionalizing the monolithic block at the outer regions to be hydrophilic so that the outer regions will be wettable. An inner region of the monolithic block can be modified or functionalized to provide the desired property or properties of what can become the inner matrix layer of the composite membrane, e.g., by functionalizing the inner region of the monolithic block to be hydrophobic so that the inner region will be dry.

In an example, chemicals can be added to one or more specified regions of the monolithic block to alter or functionalize the one or more specified regions of the monolithic block in order to form one or more layers of a composite membrane having the properties described above. In an example, a chemical (such as, for example, trimethylsilyl chloride or hexane) can be added to a middle region of the monolithic block to create an interior region or layer having hydrophobic properties. In an example, a syringe or other delivery mechanism can be used to inject one or more chemicals into select regions of the monolith. A depth that the syringe is inserted into the monolith can control what region of the monolith is modified.

The bacteria can be added to the bacteria-containing layers, such as the layers 4 and 6, before or after functionalizing the starting material. In an example, the block of starting material can be a silica gel and different regions of the silica gel can be functionalized, followed by the bacteria being migrated into the gel after curing the gel. In an example, the bacteria can be added to and encapsulated in the gel, and then the gel, with the bacteria therein, can be functionalized. In some examples where some of the bacteria can be encapsulated in portions of the gel that were intended to be the hydrophobic layer (such as the layer 8) without bacteria, once that region of the gel is functionalized to have hydrophobicity, the chemicals used for hydrophobicity can potentially kill the bacteria cells in that region, and the cells can then be washed away.

In an example, the block of material can be configured such that the composite membrane can have particular dimensions and some portions of the block have different dimensions relative to other portions of the block. In an example, the block can include an interior layer having an extended portion that is longer than other regions of the block, such as to form the membrane structures described above.

It is recognized that combinations of the methods described herein can be used to form the composite membranes and a particular combination can depend, in part, on a particular configuration of the layers in a specific composite membrane. It is recognized that additional assembly or fabrication methods for multi-layer membranes can be used as an alternative or in combination with the methods described herein.

Regardless of the assembly or fabrication method used, the layers of the composite membranes can be described as sheets, even if the layers are formed in place by depositing one or more layers on an existing layer. For example, the third layer 8 can be a sheet regardless of whether the third layer 8 is formed by three-dimensional printing or other known methods. In other examples, the layers of the composite membranes can be described as sheets, even if the layers are formed by a monolithic block and then regions modified or functionalized to create layers having desired and varying properties between layers.

FIG. 6 is a top view of an example system 30 that can include the composite membrane 2 of FIGS. 1A and 1B and a first potted manifold 32, according to an example. As shown in FIG. 6, the first layer 4 is at least partially disposed above the third layer 8 (FIG. 1A). In an example, the extended portion 9 of the third layer 8 can extend beyond the first layer 4. That is, a length of the third layer 8 can be greater than a length of the first layer 4 such that the extended portion 9 can be configured in part to attach to the manifold 32. In an example, the extended portion 9 of the third layer 8 can be exposed to an outside environment and the extended portion 9 can be free of the hydrophobic coating 5,7 (FIG. 1) or the first layer 4 or the second layer 6 (FIG. 1). In another example, the extended portion 9 can be covered by the hydrophobic coating (FIG. 2) such that the extended portion 9 can be substantially encased in the hydrophobic coating and not exposed to the outside environment.

As shown in FIG. 6, the composite membrane 2 can be potted or connected to the first manifold 32. In an example, the first manifold 32 can be configured to provide a vacuum to remove at least one of the conveyed first gas from the first layer 4 or the second conveyed gas from the second layer. The first manifold 32 can provide a constant or intermittent vacuum.

In addition to the example dimensions for the composite membrane 2 described above in reference to FIG. 1A, the composite membrane can have an overall width W1 that can be generally equal or more or less than the lengths L1 and L2. In various examples, the width W1 can be from about 0.5 meters to about 2 meters or more. In an example, the width W1 can be about 1.0 meter.

Figure 7:
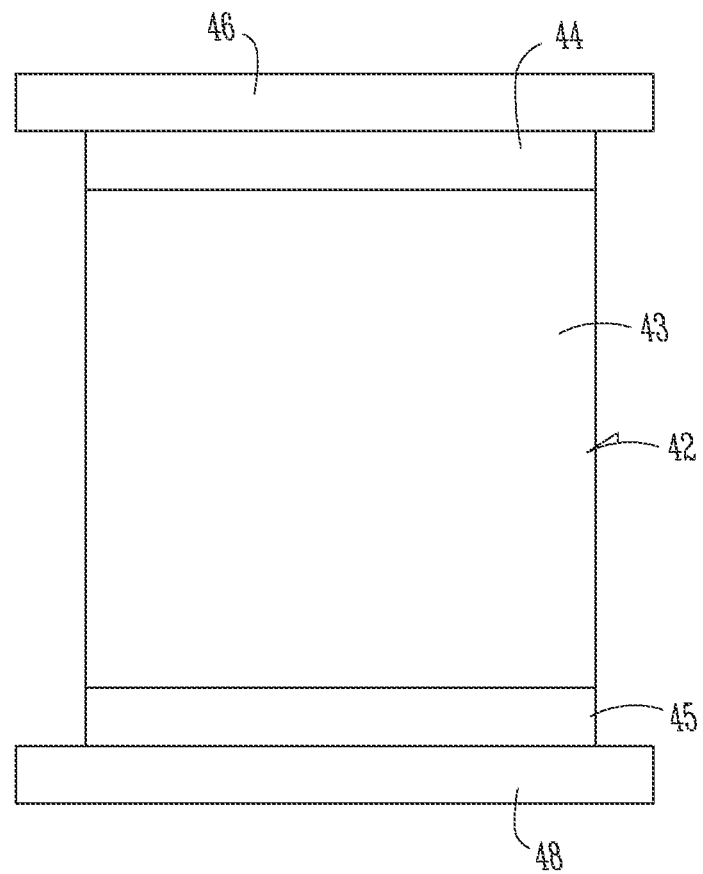
FIG. 7 is a top view of an example system including a composite membrane and two potted manifolds, in accordance with the present application.

FIG. 7 is a top view of an example system 40 that can include a composite membrane 42 potted or connected to a first 46 manifold and a second manifold 48. Similar to the composite membrane 2 of FIG. 1A, the composite membrane 42 can include a first layer 43 disposed on at least a portion of a third layer that is similar to the third layer 8 of FIG. 1A. As described in reference to FIG. 6, a first extended portion 44 of the third layer of the membrane 42 can be potted to the first manifold 46. Further, as shown in FIG. 7, a second extended portion 45 of the third layer can be potted to the second manifold 48. In an example, the second extended portion 45 can be at an end of the composite membrane 42 opposite the first extended portion 44. The composite membrane 42 can be similar to the composite membrane 2 of FIG. 1A, but the third layer in the composite membrane 42 can include an extended portion at each end of the third layer.

The second manifold 48 can be configured to provide an inert flushing gas, such that the inert flushing gas conveys the first or second produced gas to the first manifold 46 for further processing. In an example, the first manifold 46 can provide a vacuum to aid in removing the first or second produced gas from the third layer.

For example, the first extended portion 44 can be potted to the first manifold 46 and the second extended portion 45 can be potted to the second manifold 46, such that the third layer (8, FIG. 1A) is in fluid communication with the first and second manifolds 46, 48, such that inert gas can flow from the second manifold 48, through the second extended portion 45, the third layer, and the first extended portion 44 to the first manifold 46. That is, an inert gas, such as nitrogen, is provided to the second manifold 48, so as to flush the third layer, including any collected gas, and is pushed through the first manifold 46, towards further production.

It is recognized that any of the composite membranes described above and shown in FIGS. 1A-5 can be used with the manifolds of FIGS. 6 and 7.

Figure 8:
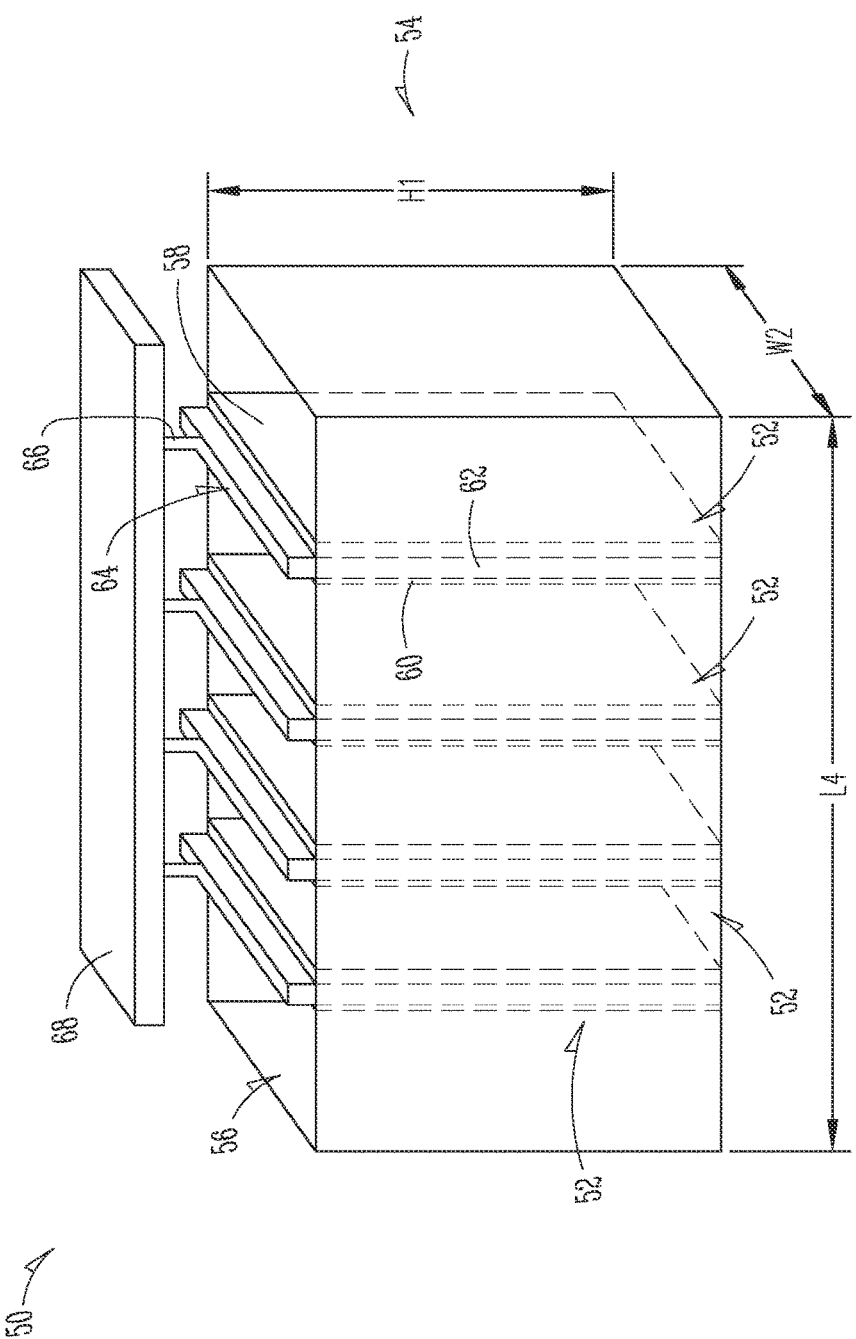
FIG. 8 is a perspective view of an example system including a plurality of membranes for wastewater generated energy and gas, in accordance with the present application.

FIG. 8 is a perspective view of a system 50 that can include a plurality of composite membranes 52 for wastewater generated energy and gas, according to an example. The composite membranes 52 can be similar to any of the composite membranes described above and shown in FIGS. 1A-5. As shown, a wastewater tank 54 can be configured to receive the plurality of composite membranes 52 within a volume 56 of the wastewater tank 54. In an example, the wastewater tank 54 can be configured to store substantially non-flowing wastewater. In another example, the wastewater tank 54 can be configured to permit the wastewater to flow through the volume 56 of the wastewater tank 54, such that the wastewater flows in contact with the plurality of composite membranes 52. In an example, the plurality of composite membranes 52 can be evenly spaced or can be unevenly spaced apart from one another. Although FIG. 8 illustrates four individual composite membranes 62, more or less membranes 62 can be included in the system 50. In an example, the system 50 can include 1, 2, 3, 4, 5, 10, 15, or more composite membranes 52.

One or more of the plurality of composite membranes 52 can include a first layer 58, a second layer 60, and a third layer 62. The first layer 58 can be similar to the first layer 4 described above in reference to the example composite membranes shown in FIGS. 1A-5. The second layer 60 can be similar to the second layer 6 described above in reference to the example composite membranes shown in FIGS. 1A-5. The third layer 62 can be similar to the third layer 8 described above in reference to the example composite membranes shown in FIGS. 1A-5. Further, one or more of the plurality of composite membranes 52 can include an extended portion 64 of the third layer 62, and the extended portion 64 can be similar to the extended portion 9 of the third layer 8 described above in reference to the example composite membranes shown in FIGS. 1A-5.

As described above, the composite membranes 52 can have any of the designs shown in FIGS. 1A-5 and described above. In an example, even though not shown in FIG. 8, one or more of the composite membranes 52 can include one or more coating layers or adhesive layers between the first layer 58 and the third layer 62 and between the second layer 60 and the third layer 62.

The extended portion 64 of the one or more of the plurality of composite membranes 52 can be potted by a connection 66 to a manifold 68. The manifold 68 can be similar to the manifold 32 or 46 shown in FIGS. 6 and 7, respectively, and described above. Although not shown in FIG. 8, in an example, the system 50 can include a second manifold similar to the second manifold 48 shown in FIG. 7 and described above. The third layer 62 of the one or more of the plurality of composite membranes 52 can be in fluid communication with the manifold 68, as described in connection with FIGS. 6-7, so as to convey a first or second produced gas to the manifold 68, for further production.

Exemplary dimensions of the composite membranes 52 are provided above in reference to FIGS. 1A and 6. It is recognized that the composite membranes 52 can be smaller or larger compared to the dimensions provided above in order to be used within the system 50. In an example, the wastewater tank 54 can have a width W2 from about 3 to 4 meters and a height H1 from about 2 to 3 meters. A length L4 of the wastewater tank 54 can depend, in part, on a number of composite membranes 52 designed for inclusion in the system 50. In an example, the length L4 can be from about 1 meter to about 10 meters.

Figure 9:
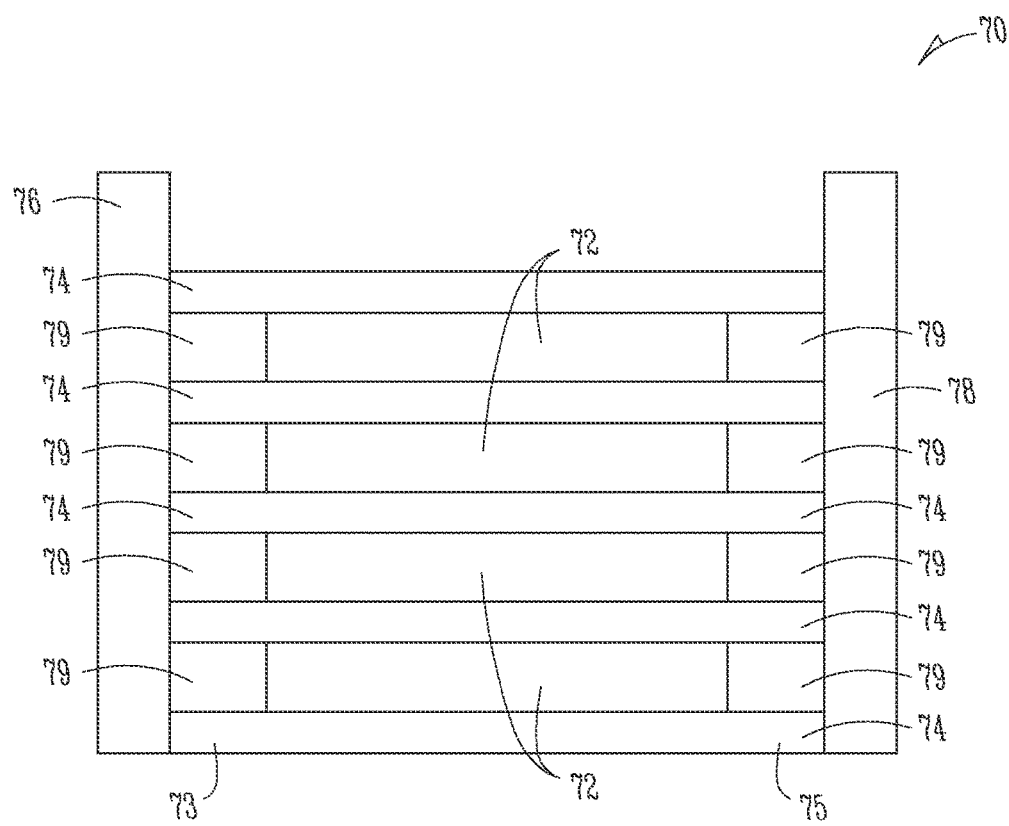
FIG. 9 is a side view of an example system for wastewater generated energy and gas, and including alternating gas-filled and bacteria-containing layers, in accordance with the present application.

FIG. 9 is a side view of a system 70 for wastewater generated energy and gas, according to an example. The system 70 can include alternating bacteria-filled layers 72 and gas-filled layers 74. The bacteria-filled layers 72 can be similar to the layers 4 or 6 described above and shown in FIGS. 1A-5. The gas-filled layers 74 can be the dry matrix layer that receives the gas produced in the bacteria-filled layers 72 and can be similar to the layer 8 described above and shown in FIGS. 1A-5. The system 70, having a plurality of bacteria filled layers 72 and a plurality of gas-filled layers 74, can provide a multi-membrane design to increase gas production from the bacteria-filled layers 72 and extraction of the gas from the gas-filled layers 74. Each of the gas-filled layers 74 can include a first extended portion 73 and a second extended portion 75, both of which can be similar to the extended portion 9 of the third layer 8 described above. The first extended portion 73 and the second extended portion 75 can be configured to attach the gas-filled layers 74 to a first manifold 76 and a second manifold 78.

A channel 79 can be formed between each neighboring pair of first extended portions 73 and between each neighboring pair of second extended portions 75. The channels 79 can be configured as wastewater channels such that the wastewater can enter the system 70 and contact the bacteria-filled layers 72. The gas-filled layers 74 can include a coating or have material properties to maintain the gas-filled layer 74 as a dry matrix such that the gas produced by the bacteria-filled layers 72 diffuses into the gas-filled layer 74, but water is prevented from wetting the gas-filled layer 74. In an example, the extended portions 73 and 75 of the gas-filled layers 74 can include a hydrophobic coating.

Other components for a composite membrane, such as the adhesive layers and hydrophobic coatings described above, are not shown in FIG. 9. However, it is recognized that the system 70 can include these other components in other examples. In the example shown in FIG. 9, the system 70 can include five gas-filled layers 74 and four bacteria-filled layers 72. It is recognized that more or less of layers 72 or layers 74 can be included in other examples. FIG. 9 shows the gas-filled layers 74 as forming the exterior layers of the system 70, but it is recognized that the exterior layers of the system 70 can also be the bacteria-filled layers 72. In other examples, the system 70 can include sealing layers that form the exterior layers of the system 70 and can be configured to prevent gas from escaping from the gas-filled layers 74.

The alternating layers 72 and 74 can be formed using any of the methods described herein for forming a composite membrane. The layers 72 and 74 can then be connected to the manifolds 76 and 78 to form the system 70.

In an example, the system 70 can be similar in size to the system 50 of FIG. 8. The bacteria-filled layers 72 and gas-filled layers 74 can have similar dimensions to the layers 4, 6 and 8 of FIG. 1A.

In an example, the system 70 or a portion of the system 70 can be placed in a wastewater tank, and thus operate, in some examples, similar to the system 50 of FIG. 8. In an example, multiple systems 70 can be used in a water tank. The system 70 can include means for providing adequate water flow through the channels 79. In an example, one side of the system 70 can be mounted to a wall of the tank and water can flow into the tank and through the channels. In an example, a pump can be used to pump water through the channels.

Figure 10A:
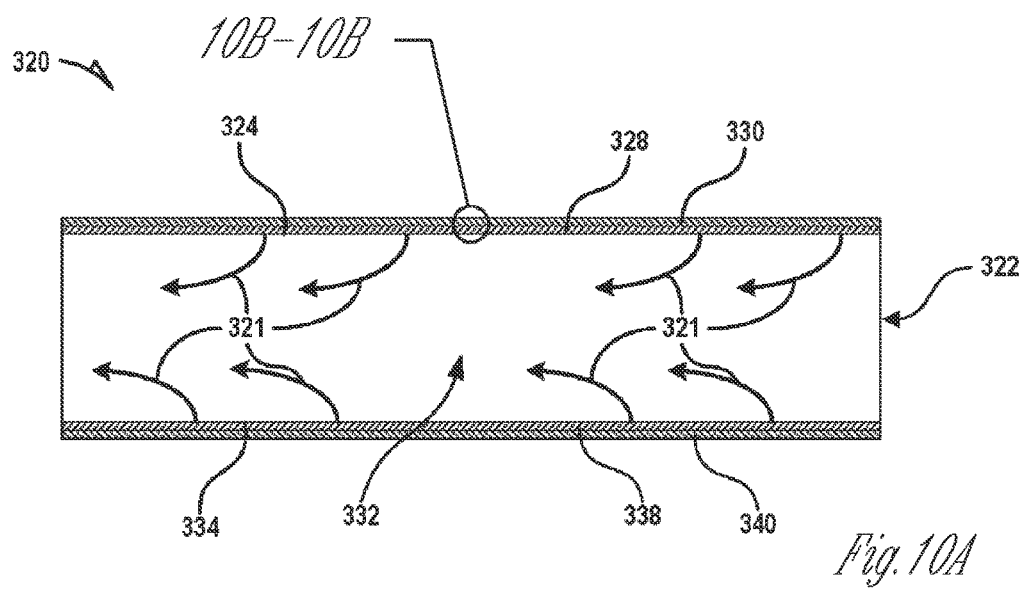
FIG. 10A is a cross-sectional side view of an example composite membrane, in accordance with the present application.
Figure 10B:
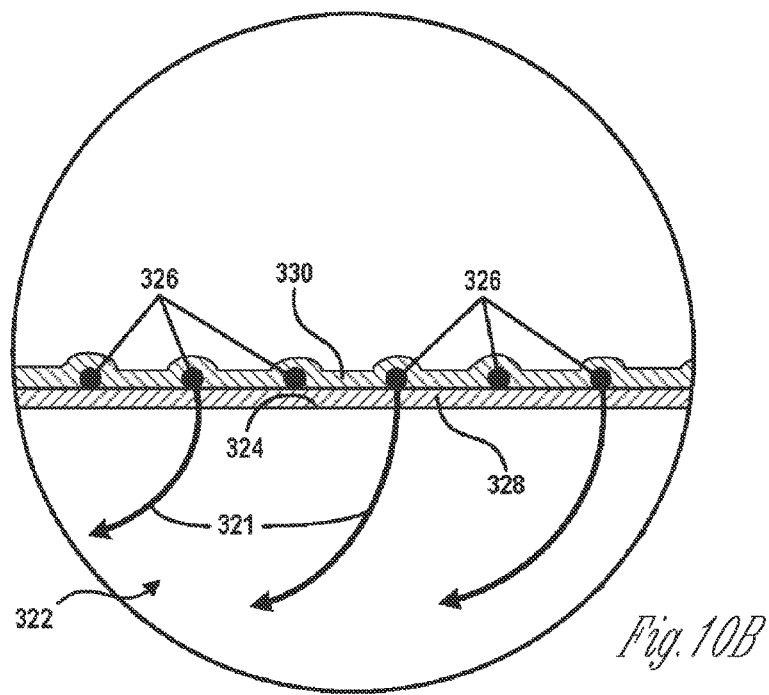
FIG. 10B is an enlarged view of a portion of the composite membrane of FIG. 10A.
Figure 11:
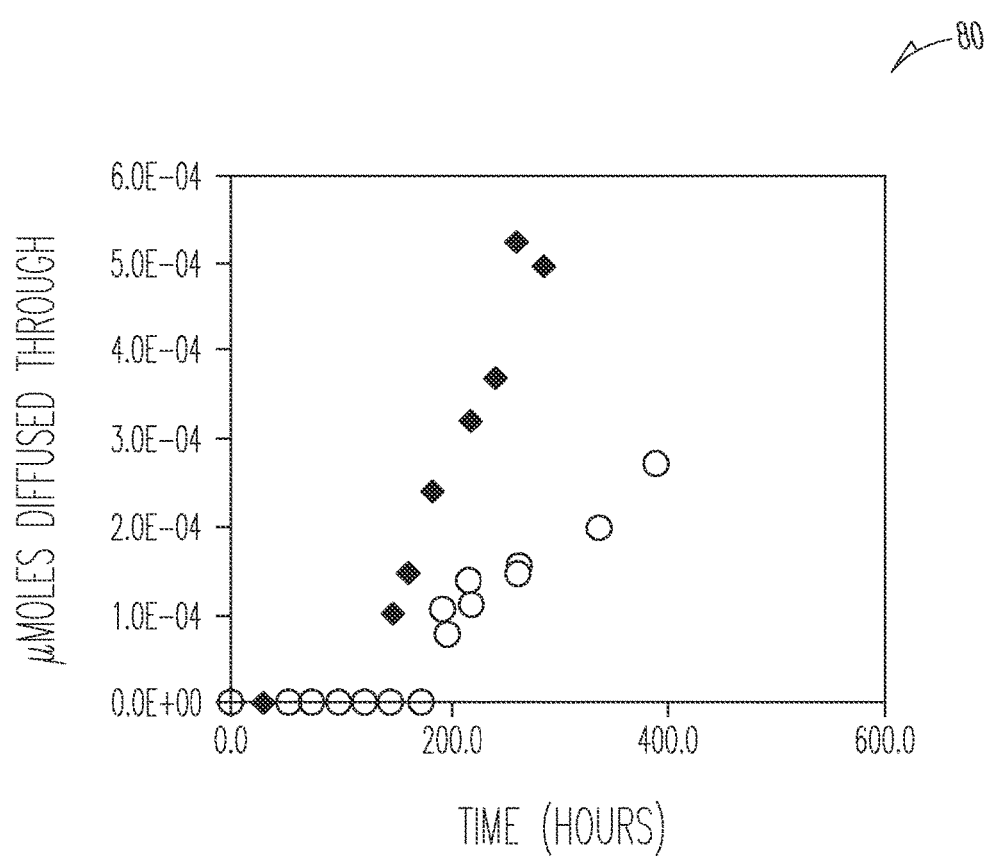
FIG. 11 is a plot of a breakthrough curve for 2,3',4',5-chlorobiphenyl diffusing through polyacrylamide, in accordance with the present application.
Figure 12:
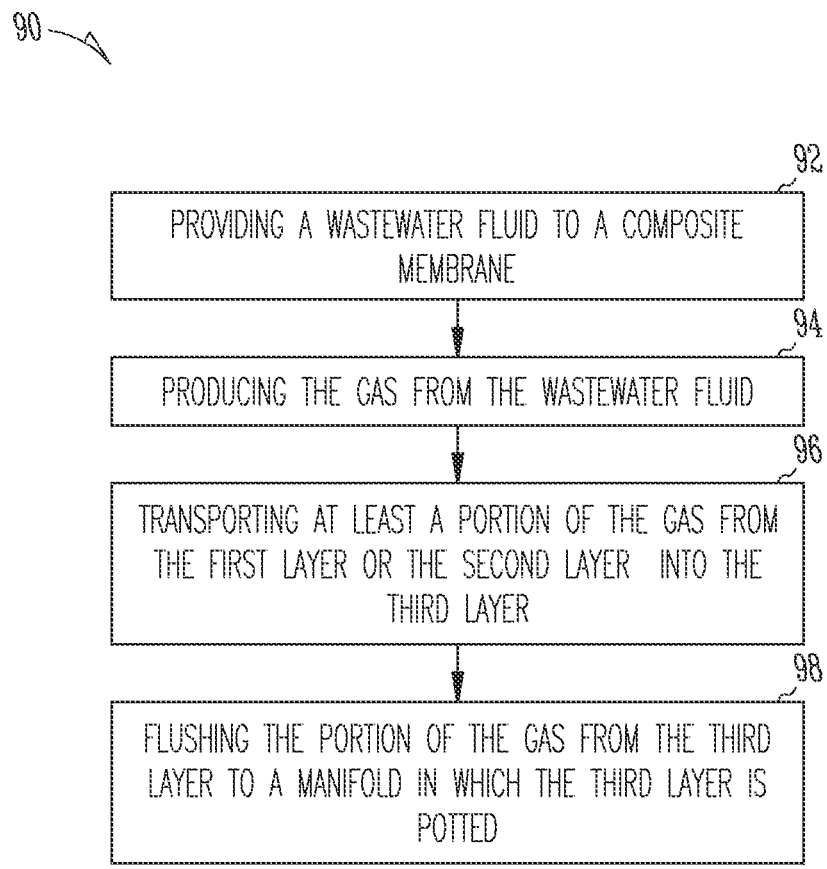
FIG. 12 is a flow chart of an example method for producing and extracting a gas from a wastewater, in accordance with the present application.
Figure 13:
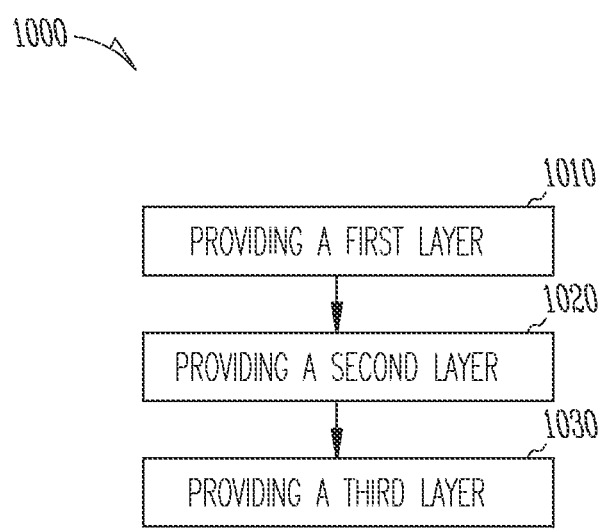
FIG. 13 is a flow chart of an example method for forming a composite membrane, in accordance with the present application.

FIGS. 10A and 10B show a cross-sectional view of another example fermentative apparatus for producing a production gas, such as one or more of hydrogen, carbon monoxide, and methane, via conversion of one or more compounds present within a wastewater stream by immobilized bacterial cells. FIG. 10B is an enlarged view of a portion of FIG. 10A taken at 10B-10B.

The example fermentative apparatus shown in FIG. 10A comprises a composite membrane 320 with a base membrane structure that can receive the production gas (shown conceptually as arrows 321 in FIG. 10A), e.g., a membrane layer 322. The membrane layer 322 can include a membrane surface 324, and bacteria cells 326 can be adhered to the membrane layer 322 at the membrane surface 324 (as shown in the magnified portion of the membrane 322 in FIG. 10B). An adhesive interface 328 at the membrane surface 324 can provide for adhesion between the bacterial cells 326 and the membrane layer 322.

The bacteria cells 326 can be similar or identical to the immobilized bacteria described above in reference to the bacteria-containing layers 4 or 6. For example, the bacteria cells 326 can be bacteria capable of converting contaminants in the wastewater stream to a more valuable production gas 321, such as one or more of hydrogen, methane, and carbon monoxide, such as one or both of acetogenic bacteria and methanogenic bacteria.

The adhesive interface 328 can immobilize the bacteria cells 326 relative to the membrane layer 322 so that the bacteria cells 326 are in a fixed position when the composite membrane 320 is exposed to a wastewater stream. The adhesive interface 328 can include an adhesive applied as an adhesive layer to the membrane surface 324 so that the adhesive is present between the membrane layer 322 and the bacteria cells 326. Examples of adhesive materials that can be used to form the adhesive interface 328 comprising a layer of adhesive can include, but are not limited to, biocompatible adhesives, such as biocompatible wet adhesives (also referred to as biocompatible waterproof or water resistant adhesives). An example of a biocompatible wet adhesive that can be used to form the adhesive interface 328 between the membrane layer 322 and the bacteria cells 326 is a polydopamine adhesive material. Other examples of adhesive material that can be used to adhere and substantially immobilize the bacteria cells 326 to the membrane layer 322 include, but are not limited to: positively-charged polyelectrolytes, such as poly-L-lysine or polyethyleneimine; and adhesive polyphenolic proteins, such as those extracted from the marine mussel *Mytilus edulisi*, for example in the adhesive formulation sold under the trade name CELL-TAK by Corning Inc. Life Sciences, Tewksbury, Mass., USA, formerly sold by BD Discovery Labware, Inc., Bedford, Mass., USA. If a positively charged polyelectrolyte is used as the adhesive material, then the material of the membrane layer 322 can be negatively charged to allow for adhesion.

An adhesive layer 328 applied to the membrane surface 324 can have a thickness selected to optimize an adhesion force, e.g., of the bacteria cells 326 to the membrane layer 322, and the diffusion of the production gas 321 from the membrane surface 324 through the membrane layer 322. In an example, the material of the adhesive layer 328 can form a substantially conformal coating onto the membrane surface 324, e.g., wherein the adhesive layer 328 substantially matches the shape of the outer surface 324 of the composite membrane 320. In examples where the membrane layer 322 is made from a porous material, e.g., as described above with respect to the third layer 8 in the composite membranes of FIGS. 1A-5, an adhesive layer 328 that forms a substantially conformal coating can conform at least partially to the pores in the membrane layer 322. In examples of a porous membrane layer 322 and a substantially conformal adhesive layer 328, the thickness of the adhesive layer 328 can be selected to be less than about one-half the size (e.g., diameter) of the pores in the membrane layer 322 so that the adhesive layer 328 will not substantially effect permeability of the production gas 321 through the pores of the membrane layer 322. For example, if the size of the pores in the membrane layer 322 are expected to be at least about 10 nanometers (nm), then the thickness of the adhesive layer 328 can be selected to be about 5 nm. In some examples with a polydopamine-based adhesive material, the thickness of the adhesive layer 328 can be from about 0.5 nm to about 50 nm, such as from about 1 nm to about 10 nm, for example about 5 nm or less.

The adhesive interface 328 can include a portion of the membrane layer 322 being chemically altered to improve adhesion between at least a portion of the membrane layer 322 and the bacteria cells 326 compared to adhesion between the membrane layer 322 and the bacteria cells 326 without the chemically-altered portion. For example, a portion of the membrane layer 322 at or proximate to the membrane surface 324 can be chemically modified so that bacteria cells 326 can adhere to the membrane surface 324. The chemical modification of the portion of the membrane layer 322 can include a surface treatment to form an adhesive surface portion of the membrane layer 322. Examples of chemical modification include, but are not limited to, modification of a hydrophilic material with one or more hydrophobic moieties and modification of a hydrophobic material with one or more hydrophilic moieties.

The composite membrane 320 can also include a sealing coat 330 applied over at least a portion of the adhesive interface 308 and the bacteria cells 306. The sealing coat 330 can include a polymer, a copolymer, a block copolymer matrix, a silica gel, or combinations thereof. The sealing coat 330 can include a material with tunable porosity, e.g., to control transfer of the water fluid through the sealing coat 330. In an example, the sealing coat 330 can include a silica-based matrix, such a matrix comprising at least one of tetramethyl orthosilicate (TMOS), tetramethylorthosilicate (TEOS), tetrakis(2-hydroxyethyl)orthosilicate (THEOS), a silica gel made out of a silica precursor with hydrolysable side groups, or another silica-based compound or compounds. The silica-based compound or compounds of the matrix can also be cross-linked with one or more materials that can enhance the sealing coat 330, including, but not limited to, crosslinking to silica nanoparticles. In an example, the sealing coat 330 can comprise, in place of or in addition to the silica-based matrices described above, at least one of poly(vinyl alcohol), polyacrylamide, poly(ethylene oxide), polypropylene oxide, latex, nylon, and Pluronic F127 dimethacrylate.

The sealing coat 330 can have a thickness that is selected to optimize mass transfer of the compounds from the wastewater fluid through the sealing coat 330 so that the compounds can be accessed by the bacteria cells 326. The thickness of the sealing coat 330 can also be selected to balance the mass transfer of these compounds and the overall structural integrity of the composite membrane 320, e.g., with a thicker sealing coat 330 potentially providing for relatively less mass transfer but relatively higher structural integrity (e.g., rigidity, toughness, etc.). In an example, the thickness of the sealing coat 330 can be from about 0.01 millimeters (mm) to about 2 mm, such as from about 0.1 mm to about 1 mm.

As shown in FIGS. 10A and 10B, a first adhesive interface 328 can be applied to a first membrane surface 324 for adhesion of bacteria cells 326, and then a first sealing coat 330 can be applied over the adhesive interface 328 and the bacteria cells 326 to further secure the bacteria cells 326 to the membrane layer 322. The generally planer membrane layer 322 can also include a second membrane surface 334 that is generally opposed to the first membrane surface 324. A second adhesive interface 338 can be applied to the second membrane surface 334 and a second set of bacteria cells (not shown) can be adhered to the second membrane surface 334 in substantially the same manner as the bacteria cells 326 to the first adhesive interface 328. The second adhesive interface 338 can be substantially identical to the first adhesive interface 328 described above. The second set of bacteria cells can be substantially identical to the bacteria cells 326 described above. A second sealing coat 340 can be applied over at least a portion of the second adhesive interface 338 and the second bacteria cells. The second sealing coat 340 can be substantially identical to the first sealing coat 330 described above. In this way, the composite membrane 320 can be referred to a "sandwich structure," in much the same way as the sandwich structure of the composite membranes described above in reference to FIGS. 1A-5. However, the ability to immobilize the bacteria cells 326 directly to, or substantially directly to, the membrane surfaces 324, 334 can allow for better capture of the production gas by the membrane structure 322 because of the close proximity of the bacteria cells 326 to the membrane structure 322.

As with the systems described above, the composite membrane 320 of FIGS. 10A-10B can include structures or systems for removal of the production gas from the membrane structure 322. For example, one or more ends of the membrane layer 322 can be potted in one or more manifolds, similar to the composite membranes being potted to the manifolds described with respect to FIGS. 6-9.

In an example, a manifold into which the membrane structure is potted can be configured to apply a vacuum to remove the production gas from the membrane layer 322. For example, the vacuum applied to the manifold can draw the production gas from an interior volume 332 of the membrane layer 322. In an example, a manifold into which the membrane structure is potted can be configured to provide an inert flushing gas to the membrane layer 322. In an example, a manifold can feed an inert flushing gas to the interior volume 332 of the membrane layer 322 to drive the production gas through membrane layer 322 for removal. In an example, a first manifold can provide an inert flushing gas to the membrane layer 322 and a second manifold can provide for removal of the production gas and the inert flushing gas, e.g., by applying a vacuum to the membrane layer 322 via the second manifold.

The composite membrane 320 can be prepared by immobilizing the bacteria cells 326 onto the membrane surface 324, 334, e.g., by applying an adhesive to the membrane surface 324, 334 to form an adhesive interface 328, 338 for adhesion of the bacteria cells 326. In an example, a solution of adhesive material, such as a solution comprising polydopamine (PDA) can be made and applied to each membrane surface 324, 334, such as by applying the PDA solution to the surfaces 324, 334 of the membrane layer 322. In an example, a PDA solution can be made by dissolving dopamine hydrochloride in a solvent solution. In an example, the solvent solution includes tris(hydroxymethyl)aminomethane (chemical formula $(HOCH_2)_3CNH_2$) also referred to as "Tris." In an example, the Tris solution has a pH of about 8.5. The PDA solution can be applied to the membrane layer 322 by any suitable method of applying a liquid composition to form a thin layer, such as dip coating, spray coating, spin coating, and the like. In an example, the membrane layer 322 can be dip-coated in the PDA solution to form a thin film of PDA adhesive on the surfaces 324, 334. In an example, the PDA film on the membrane layer 322 can have a thickness of 50 nanometers (nm) or less.

The thin layer of the adhesive film can form the adhesive interface 328, 338 that can provide an adhesive surface for the bacteria cells 326. The bacteria cells 326 can be applied by providing or receiving a concentrated cell culture of the bacteria cells 326 that can be applied onto adhesive surfaces formed by the adhesive interfaces 328, 338 on the membrane layer 322. In an example, the concentrated cell culture can be sprayed onto the membrane layer 322, such as by spraying the concentrated cell culture onto each side of the membrane layer 322 that has been at least partially coated with the PDA adhesive to form the adhesive interfaces 328, 338. The concentration of the bacteria cells 326 in the culture can be selected and controlled based on the sprayed volume of the culture in order to achieve a desired concentration of the bacteria cells 326 on the membrane surface or surfaces 324, 334. In an example, the concentration of the bacteria cells 326 applied to the surfaces 324, 334 can be from about 0.1 micrograms of the cells/square cm (μg/cm2) to about 100 μg/cm2, such as from about 0.5 μg/cm2 to about 30 μg/cm2.

The membrane structure 302, 322 can then be allowed to dry, such as by air drying, to allow the bacteria cells 326 to adhesively bond to the adhesive interfaces 328, 338, and thus to the membrane surface or surfaces 324, 334. After drying, a sealing coat 330, 340 can be applied. In an example method, the sealing coat 330, 340 can be formed by applying a silica-based gel over the adhesive interfaces 328, 338 formed on the membrane layer 322 and the adhered bacteria cells 326. For example, the membrane layer 322 with the bacteria cells 326 adhered thereto with an adhesive interface 328, 338 can be dip-coated with a silica gel, such as a silica gel comprising silica nanoparticles cross-linked with tetraethyl orthosilicate (TEOS) cross-linked silica nanoparticles (e.g., TEOS cross-linked colloidal nanoparticles sold under the trade name LUDOX TM40 by Sigma-Aldrich Co, LLC., St. Louis, Mo., USA). The ratio of the TEOS to the silica nanoparticles can be about 3:1 (v/v).

In an example, the composite membrane 320 can be usable in the systems shown in FIGS. 6-9 and described above. The composite membrane 320 can be assembled or made using the methods described above or a combination thereof.

Reference is made to U.S. Provisional Patent Application No. 62/241,910, filed on Oct. 15, 2015, entitled "MEMBRANES FOR WASTEWATER-GENERATED ENERGY AND GAS," the entire disclosure of which is hereby expressly incorporated by reference herein, which discloses the composite membrane 320.

FIG. 11 is a plot 80 of a breakthrough curve for 2,3',4',5-chlorobiphenyl diffusing through polyacrylamide, according to an example. The plot 80 indicates that composite membranes containing bacteria capable of degrading 2,3',4',5-chlorobiphenyl increase the time to 2,3',4',5-chlorobiphenyl breakthrough and its subsequent flux through the composite membrane. Such information is used to model or configure membrane thicknesses, such as during casting or extrusion to provide that the diffusion from the cell surface toward a gas-filled layer (8, FIG. 1A) is preferred over diffusion toward the solution in the reactor and to optimize the quantity of bacteria immobilized in the polymer. Polyacrylamide is an example of a hydrophilic polymer that could be used for the immobilization of the bacteria.

FIG. 12 is a flow chart illustrating a method 90 for producing and extracting a gas from a wastewater, according to an example. At 92, the method 90 includes providing a wastewater fluid to a composite membrane, such as the composite membranes described in reference to FIGS. 1A-5. In an example, the membrane can be substantially immersed in the wastewater, such as in a wastewater tank, similar to the wastewater tank 54 shown in FIG. 8. In an example where the wastewater is at rest, the system can be configured to operate in batch mode, so as to treat discrete amounts of water. Additionally, in an example, the system is configured to operate in a continuous or flow through mode. In the flow through mode, a residence time or membrane area is altered to maximize treated water quality or gas production. The residence time is altered by adjusting the wastewater tank or reactor volume or adjusting a flow rate of the wastewater through or around the membrane. The composite membrane can include a first layer and a second layer each including immobilized bacteria, wherein the immobilized bacteria are configured to produce a gas from one or more compounds in a wastewater fluid. Further, the composite membrane of the method 90 can include a third layer at least partially disposed between the first layer and the second layer, the third layer configured to receive the gas.

At 94, the gas is produced from the wastewater fluid, such as by the immobilized bacteria. For example, the immobilized bacteria can produce the gas from at least one of acetogenesis and methanogenesis, as described herein. At, 96, at least a portion of the produced gas is transported from the wastewater into the third layer. For example, the produced gas can diffuse through a hydrophobic coating over at least a portion of the third layer, as described herein.

At 98, the method 90 includes flushing the portion of the gas from the third layer to a manifold, wherein the third layer is potted to the manifold. As used herein, flushing can include applying a vacuum to the third layer, such as by the manifold, to flush the portion of the produced gas from the third layer. In an example, the third layer is flushed with an inert gas, such as nitrogen. The inert gas is pumped from a second manifold (48, FIG. 7) to a first manifold (46, FIG. 7). The inert gas can be provided to the second manifold, through the third layer, and to the first manifold for further processing. In an example, the inert gas can be provided to the second manifold and the first manifold can apply a vacuum.

The method 90 for producing and extracting a gas from wastewater can be used with any of the composite membranes and systems described herein. The composite membrane can include any of the membranes shown in FIGS. 1A-5, 10A and 10B, which can be configured in the systems shown in FIGS. 6-9. In an example, the composite membrane can be a sandwich configuration with the first, second and third layers 4, 6 and 8 described above. In an example, the composite membrane can include alternating bacteria-filled layers and gas-filled layers, as described above in reference to the system 70 of FIG. 9.

FIG. 13 is a flow chart illustrating a method 1000 for forming a composite membrane, according to an example. At 1010, the method can include providing a first layer containing immobilized bacteria. At 1020, the method can include providing a second layer containing immobilized bacteria. At 1030, the method can include providing a third layer that can be at least partially disposed between the first layer and the second layer. The third layer can be a dry matrix layer and configured as a gas-filled layer such that the gas produced by the bacteria in the first and second layers can diffuse to the third layer, and then be extracted from the membrane.

Providing a first layer in 1010 can include providing one or more adhesives or coatings with the first layer such that one or more adhesive or coating layers can be disposed between the first layer and the third layer. Similarly, providing a second layer in 1020 can include providing one or more adhesives or coatings with the second layer such that one or more adhesive or coating layers can be disposed between the second layer and the third layer.

Providing the first, second and third layers in 1010, 1020 and 1030 can include stacking the first, second and third layers, depositing one or more of the layers on top of one another, starting with a single block of material to form the first, second and third layers, or a combination thereof, as described above. Providing the first, second and third layers in 1010, 1020 and 1030 can include functionalizing one or more of the first, second and third layers such that the layers can be formed from the same starting material and functionalized to have different material properties (such as, for example, hydrophobicity) relative to one another.

The method 1000 can include additional steps such as providing more layers in combination with the first, second and third layers. In an example, providing the first layer in 1010 can include providing an additional outer layer configured to be disposed on the first layer opposite the third layer (see FIG. 5). In an example, additional layers can be provided to form the alternating configuration of bacteria-containing layers and gas-filled layers of the system 70 shown in FIG. 9.

In this document, the terms "a," "an," or "the" are used to include one or more than one unless the context clearly dictates otherwise. The term "or" is used to refer to a nonexclusive "or" unless otherwise indicated. In addition, it is to be understood that the phraseology or terminology employed herein, and not otherwise defined, is for the purpose of description only and not of limitation. Any use of section headings is intended to aid reading of the document and is not to be interpreted as limiting; information that is relevant to a section heading can occur within or outside of that particular section. Furthermore, all publications, patents, and patent documents referred to in this document are incorporated by reference herein in their entirety, as though individually incorporated by reference. In the event of inconsistent usages between this document and those documents so incorporated by reference, the usage in the incorporated reference should be considered supplementary to that of this document; for irreconcilable inconsistencies, the usage in this document controls.

Although the invention has been described with reference to specific example embodiments, it will be evident that various modifications and changes can be made to these embodiments without departing from the broader spirit and scope of the invention. Accordingly, the specification and drawings are to be regarded in an illustrative rather than a restrictive sense. The accompanying drawings that form a part hereof, show by way of illustration, and not of limitation, specific embodiments in which the subject matter can be practiced. The embodiments illustrated are described in sufficient detail to enable those skilled in the art to practice the teachings disclosed herein. Other embodiments can be utilized and derived therefrom, such that structural and logical substitutions and changes can be made without departing from the scope of this invention. This Detailed Description, therefore, is not to be taken in a limiting sense, and the scope of various embodiments is defined only by the appended claims, along with the full range of equivalents to which such claims are entitled.

Such embodiments of the inventive subject matter can be referred to herein, individually and/or collectively, by the term "invention" merely for convenience and without intending to voluntarily limit the scope of this application to any single invention or inventive concept if more than one is in fact disclosed. Thus, although specific embodiments have been illustrated and described herein, it should be appreciated that any arrangement calculated to achieve the same purpose can be substituted for the specific embodiments shown. This invention is intended to cover any and all adaptations or variations of various embodiments. Combinations of the above embodiments, and other embodiments not specifically described herein, will be apparent to those of skill in the art upon reviewing the above description.

The present application provides for the following exemplary embodiments or examples, the number of which is not to be construed as designating levels of importance:

Example 1 provides an apparatus for producing a gas from a wastewater fluid and can comprise a first layer including a first immobilized bacteria, wherein the first immobilized bacteria are configured to produce a first gas from one or more compounds in a wastewater fluid, a second layer including a second immobilized bacteria, wherein the second immobilized bacteria are configured to produce a second gas from the one or more compounds in the wastewater fluid, and a third layer at least partially disposed between the first layer and the second layer, the third layer configured to receive at least one of the first gas and the second gas from the first layer and the second layer, respectively.

Example 2 provides the apparatus of Example 1 optionally configured such that the first gas or the second gas includes at least one of hydrogen, carbon dioxide, and methane.

Example 3 provides the apparatus of Example 1 or 2 optionally configured such that the first immobilized bacteria and the second immobilized bacteria include at least one of acetogenic bacteria and methanogenic bacteria.

Example 4 provides the apparatus of any of Examples 1-3 optionally further comprising a hydrophobic coating disposed over at least a portion of the third layer, wherein the hydrophobic coating is configured to permit passage of at least one of the first gas and the second gas from the first layer and second layer, respectively, into the third layer.

Example 5 provides the apparatus of any of Examples 1-4 optionally configured such that one or more of the first layer, the second layer, and the third layer comprise at least one of poly(vinyl alcohol), polyacrylamide, poly(ethylene oxide), polypropylene oxide, latex, nylon, Pluronic F127 dimethacrylate, tetramethyl orthosilicate (TMOS), Tetramethylorthosilicate (TEOS), Tetrakis(2-hydroxyethyl)orthosilicate, (THEOS) or a silica gel made out of any other silica precursor with hydrolysable sidegroups, or combinations thereof.

Example 6 provides the apparatus of any of Examples 1-5 optionally configured such that the first layer, the second layer, and the third layer are formed of substantially the same material prior to adding the first and second immobilized bacteria to the first layer and the second layer, respectively.

Example 7 provides the apparatus of any of Examples 1-6 optionally configured such that at least one of the first immobilized bacteria and the second immobilized bacteria are encapsulated in a silica-based matrix.

Example 8 provides the apparatus of any of Examples 1-7 optionally configured such that the third layer includes a first extended portion not disposed between the first layer and the second layer.

Example 9 provides the apparatus of Example 8 optionally configured such that a hydrophobic coating is disposed over the first extended portion.

Example 10 provides the apparatus of Example 8 optionally configured such that the first extended portion is configured to be in fluid communication with a first manifold.

Example 11 provides the apparatus of Example 10 optionally configured such that the third layer includes a second extended portion opposite the first extended portion and not disposed between the first layer and the second layer, the second extended portion configured to be in fluid communication with a second manifold, and wherein the second manifold is configured to provide an inert flushing gas to the third layer.

Example 12 provides the apparatus of any of Examples 1-11 optionally further comprising at least one of a first adhesive layer disposed between the first layer and the third layer, and a second adhesive layer disposed between the second layer and the third layer.

Example 13 provides the apparatus of Example 12 optionally configured such that at least one of the first adhesive layer and the second adhesive layer comprises polydopamine.

Example 14 provides the apparatus of any of Examples 1-13 optionally further comprising at least one of a first outer layer disposed on the first layer opposite to the third layer, and a second outer layer disposed on the second layer opposite to the third layer, wherein the first outer layer and the second outer layer are formed of the same material as the first layer and the second layer, respectively, prior to adding the first and second immobilized bacteria to the first layer and the second layer, respectively.

Example 15 provides a system for producing and extracting a gas from a wastewater and can comprise a plurality of composite membranes, each composite membrane including a first layer including a first immobilized bacteria, wherein the first immobilized bacteria are configured to produce a first gas from one or more compounds in a wastewater fluid, a second layer including a second immobilized bacteria, wherein the second immobilized bacteria are configured to produce a second gas from the one or more compounds in the wastewater fluid, and a third layer at least partially disposed between the first layer and the second layer, the third layer configured to receive at least one of the first gas and the second gas. The system can further comprise a wastewater tank configured to receive the plurality of composite membranes and the wastewater and a manifold in fluid communication with each of the plurality of composite membranes. The wastewater tank can provide contact between the wastewater and the first layer of each of the composite membranes and contact between the wastewater and the second layer of each of the composite membranes. The manifold can be configured to extract the first and second gas from the third layer of each of the composite membranes.

Example 16 provides a method for producing and extracting a gas from a wastewater and can comprise providing a wastewater fluid to a composite membrane. The composite membrane can include a first layer and a second layer each including an immobilized bacteria, wherein the immobilized bacteria are configured to produce a gas from one or more compounds in a wastewater fluid, and a third layer at least partially disposed between the first layer and the second layer, the third layer configured to receive the gas from the first and second layers. The method can further comprise producing the gas in the first and second layers using the one or more compounds in the wastewater fluid, transporting at least a portion of the gas from the first layer and the second layer into the third layer, and extracting the gas from the third layer.

Example 17 provides the method of Example 16 optionally configured such that the third layer is configured to be hydrophobic and the first and second layers are configured to be hydrophilic.

Example 18 provides the method of Example 16 or 17 optionally configured such that at least one of a coating or an adhesive is disposed between the first layer and the third layer and between the second layer and the third layer.

Example 19 provides the method of any of Examples 16-18 optionally configured such that producing the gas comprises at least one of acetogenesis and methanogenesis.

Example 20 provides the method of any of Examples 16-19 optionally configured such that the third layer is in fluid communication with a manifold, and extracting the gas from the third layer includes flushing the gas from the third layer to the manifold.

Example 21 provides the method of any of Examples 16-20 optionally configured such that extracting the gas comprises vacuuming the gas from the third layer through the manifold.

Example 22 provides the method of any of Examples 16-21 optionally configured such that extracting the gas comprises pumping an inert gas through the third layer.

Example 23 provides the method of any of Examples 16-22 optionally further comprising adjusting a residency time that the wastewater is in contact with the composite membrane.

Example 24 provides a composite membrane for producing a gas from a wastewater fluid and can comprise a plurality of bacteria-containing layers arranged in parallel to one another, each bacteria-containing layer including immobilized bacteria configured to produce a gas from one or more compounds in a wastewater fluid. The composite membrane can further comprise a plurality of gas-filled layers arranged in parallel to one another. A gas-filled layer can be disposed between each adjacent pair of bacteria-containing layers such that the composite membrane includes a pattern of alternating bacteria-containing layers and gas-filled layers. The plurality of gas-filled layers can be configured to receive the gas produced by the immobilized bacteria in the bacteria-containing layers.

Example 25 provides the composite membrane of Example 24 optionally further comprising a manifold connected to each of the plurality of gas-filled layers, the manifold configured to remove the gas from the gas-filled layers.

Example 26 provides the composite membrane of Example 24 or 25 optionally configured such that the plurality of bacteria-containing layers and the plurality of gas-filled layers are formed from a block of starting material, and the gas-filled layers are altered to have hydrophobic properties.

The Abstract of the Invention is provided to comply with 37 C.F.R. § 1.72(b), requiring an abstract that will allow the reader to quickly ascertain the nature of the technical invention. It is submitted with the understanding that it will not be used to interpret or limit the scope or meaning of the claims. In addition, in the foregoing Detailed Description, it can be seen that various features are grouped together in a single embodiment for the purpose of streamlining the invention. This method of invention is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separate embodiment.

Various aspects of the disclosure have been described. These and other aspects are within the scope of the following claims.

What is claimed is:

1. An apparatus for producing a gas from a wastewater fluid, the apparatus comprising:
 a first layer including a first immobilized bacteria, wherein the first immobilized bacteria are configured to produce a first gas from one or more compounds in a wastewater fluid;
 a second layer including a second immobilized bacteria, wherein the second immobilized bacteria are configured to produce a second gas from the one or more compounds in the wastewater fluid; and
 a third layer at least partially disposed between the first layer and the second layer, the third layer configured to receive at least one of the first gas and the second gas from the first layer and the second layer, respectively.

2. The apparatus of claim 1, wherein the first gas or the second gas includes at least one of hydrogen, carbon dioxide, and methane.

3. The apparatus of claim 1, wherein the first immobilized bacteria and the second immobilized bacteria each comprise at least one of acetogenic bacteria and methanogenic bacteria.

4. The apparatus of claim 1, further comprising a hydrophobic coating disposed over at least a portion of the third layer, wherein the hydrophobic coating is configured to permit passage of at least one of the first gas and the second gas from the first layer and second layer, respectively, into the third layer.

5. The apparatus of claim 1, wherein one or more of the first layer, the second layer, and the third layer comprise at least one of poly(vinyl alcohol), polyacrylamide, poly(ethylene oxide), polypropylene oxide, latex, nylon, poloxamer, tetramethyl orthosilicate (TMOS), Tetramethylorthosilicate (TEOS), Tetrakis(2-hydroxyethyl)orthosilicate (THEOS), a silica gel, or combinations thereof.

6. The apparatus of claim 1, wherein the first layer, the second layer, and the third layer are formed of substantially the same material prior to adding the first and second immobilized bacteria to the first layer and the second layer, respectively.

7. The apparatus of claim 1, wherein at least one of the first immobilized bacteria and the second immobilized bacteria are encapsulated in a silica-based matrix.

8. The apparatus of claim 1, wherein the third layer includes a first extended portion not disposed between the first layer and the second layer.

9. The apparatus of claim 8, wherein a hydrophobic coating is disposed over the first extended portion.

10. The apparatus of claim 8, wherein the first extended portion is configured to be in fluid communication with a first manifold.

11. The apparatus of claim 10, wherein the third layer includes a second extended portion opposite the first extended portion and not disposed between the first layer and the second layer, the second extended portion configured to be in fluid communication with a second manifold, and wherein the second manifold is configured to provide an inert flushing gas to the third layer.

12. The apparatus of claim 1, further comprising at least one of a first adhesive layer disposed between the first layer and the third layer, and a second adhesive layer disposed between the second layer and the third layer.

13. The apparatus of claim 12, wherein at least one of the first adhesive layer and the second adhesive layer comprises polydopamine.

14. The apparatus of claim 1, further comprising at least one of a first outer layer disposed on the first layer opposite to the third layer, and a second outer layer disposed on the second layer opposite to the third layer, wherein the first outer layer and the second outer layer are formed of the same material as the first layer and the second layer, respectively, prior to adding the first and second immobilized bacteria to the first layer and the second layer, respectively.

15. A system for producing and extracting a gas from a wastewater, the system comprising:
 a plurality of composite membranes, each composite membrane including:
 a first layer including a first immobilized bacteria, wherein the first immobilized bacteria are configured to produce a first gas from one or more compounds in a wastewater fluid;
 a second layer including a second immobilized bacteria, wherein the second immobilized bacteria are configured to produce a second gas from the one or more compounds in the wastewater fluid; and
 a third layer at least partially disposed between the first layer and the second layer, the third layer configured to receive at least one of the first gas and the second gas;
 a wastewater tank configured to receive the plurality of composite membranes and the wastewater, wherein the wastewater tank provides contact between the wastewater and the first layer of each of the composite membranes and contact between the wastewater and the second layer of each of the composite membranes; and
 a manifold in fluid communication with each of the plurality of composite membranes, wherein the manifold is configured to extract the first and second gas from the third layer of each of the composite membranes.

16. A method for producing and extracting a gas from a wastewater, the method comprising:
 providing a wastewater fluid to a composite membrane, the composite membrane comprising:
 a first layer and a second layer each including an immobilized bacteria, wherein the immobilized bacteria are configured to produce a gas from one or more compounds in a wastewater fluid; and
 a third layer at least partially disposed between the first layer and the second layer, the third layer configured to receive the gas from the first and second layers;
 producing the gas in the first and second layers using the one or more compounds in the wastewater fluid;
 transporting at least a portion of the gas from the first layer and the second layer into the third layer; and
 extracting the gas from the third layer.

17. The method of claim 16, wherein the third layer is configured to be hydrophobic and the first and second layers are configured to be hydrophilic.

18. The method of claim 16, wherein at least one of a coating or an adhesive is disposed between the first layer and the third layer and between the second layer and the third layer.

19. The method of claim 16, wherein producing the gas comprises at least one of acetogenesis and methanogenesis.

20. The method of claim 16, wherein the third layer is in fluid communication with a manifold, and extracting the gas from the third layer includes flushing the gas from the third layer to the manifold.

* * * * *

UNITED STATES PATENT AND TRADEMARK OFFICE
CERTIFICATE OF CORRECTION

PATENT NO. : 10,035,719 B2
APPLICATION NO. : 14/884407
DATED : July 31, 2018
INVENTOR(S) : Novak et al.

It is certified that error appears in the above-identified patent and that said Letters Patent is hereby corrected as shown below:

On the Title Page

On page 3, in Column 1, under "Other Publications", Line 64, delete "Biornolecules" and insert --Biomolecules-- therefor In the Specification In Column 4, Line 52, delete "second 6 layer" and insert --second layer 6-- therefor In Column 5, Line 48, delete "tetramethylorthosilicate" and insert --tetraethyl orthosilicate-- therefor In Column 6, Line 10, delete "electro spinning," and insert --electrospinning,-- therefor In Column 7, Line 14, delete "Tetramethylorthosilicate" and insert --Tetraethyl orthosilicate-- therefor In Column 7, Line 24, delete "Tetramethylorthosilicate" and insert --Tetraethyl orthosilicate-- therefor In Column 7, Line 49, delete "electro spinning" and insert --electrospinning-- therefor In Column 10, Line 49, delete "2" and insert --4-- therefor In Column 10, Line 50, delete "4" and insert --6-- therefor In Column 11, Line 32, delete "third layer" and insert --first layer-- therefor In Column 15, Line 28, delete "first 46 manifold" and insert --first manifold 46-- therefor In Column 15, Line 51, delete "46," and insert --48,-- therefor In Column 16, Line 13, delete "62," and insert --52,-- therefor Signed and Sealed this
Third Day of December, 2019

Andrei Iancu
*Director of the United States Patent and Trademark Office*

CERTIFICATE OF CORRECTION (continued)
U.S. Pat. No. 10,035,719 B2

In Column 16, Line 14, delete "62" and insert --52-- therefor

In Column 17, Line 4, delete "bacteria filled" and insert --bacteria-filled-- therefor In Column 18, Line 5, delete "membrane" and insert --membrane layer-- therefor In Column 19, Line 25, delete "308" and insert --328-- therefor In Column 19, Line 25, delete "306." and insert --326.-- therefor In Column 19, Line 29, delete "water" and insert --wastewater-- therefor In Column 19, Line 32, delete "tetramethylorthosilicate" and insert --tetraethyl orthosilicate-- therefor In Column 20, Line 55, delete "(HOCH2)3CNH2)" and insert --(HOCH$_2$)$_3$CNH$_2$)-- therefor In Column 24, Lines 43-44, delete "Tetramethylorthosilicate" and insert --Tetraethyl orthosilicate-- therefor In the Claims In Column 27, Line 40, in Claim 5, delete "Tetramethylorthosilicate" and insert --Tetraethyl orthosilicate-- therefor